United States Patent
Antoulinakis et al.

(10) Patent No.: US 9,645,153 B2
(45) Date of Patent: *May 9, 2017

(54) LABELING REAGENTS AND METHODS OF THEIR USE

(71) Applicant: LIFE TECHNOLOGIES CORPORATION, Carlsbad, CA (US)

(72) Inventors: Evan Antoulinakis, Tonawanda, NY (US); Kyle Gee, Springfield, OR (US); Aleksey Rukavishnikov, Eugene, OR (US)

(73) Assignee: Life Technologies Corporation, Carlsbad, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/829,346

(22) Filed: Aug. 18, 2015

(65) Prior Publication Data

US 2015/0355186 A1    Dec. 10, 2015

Related U.S. Application Data

(63) Continuation of application No. 13/972,081, filed on Aug. 21, 2013, now Pat. No. 9,140,706, which is a continuation of application No. 12/023,019, filed on Jan. 30, 2008, now Pat. No. 8,586,743.

(60) Provisional application No. 60/887,218, filed on Jan. 30, 2007.

(51) Int. Cl.

| | |
|---|---|
| G01N 33/58 | (2006.01) |
| C07D 311/18 | (2006.01) |
| C07D 495/22 | (2006.01) |
| C07D 493/14 | (2006.01) |
| C07D 209/18 | (2006.01) |
| C07F 5/02 | (2006.01) |
| C09B 11/26 | (2006.01) |
| C09B 45/00 | (2006.01) |
| C07D 311/82 | (2006.01) |
| G01N 33/532 | (2006.01) |
| C07D 401/10 | (2006.01) |
| C07D 209/14 | (2006.01) |

(52) U.S. Cl.
CPC ........... *G01N 33/58* (2013.01); *C07D 209/14* (2013.01); *C07D 209/18* (2013.01); *C07D 311/18* (2013.01); *C07D 311/82* (2013.01); *C07D 401/10* (2013.01); *C07D 493/14* (2013.01); *C07D 495/22* (2013.01); *C07F 5/022* (2013.01); *C09B 11/26* (2013.01); *C09B 45/00* (2013.01); *G01N 33/532* (2013.01); *G01N 33/582* (2013.01)

(58) Field of Classification Search
CPC .... G01N 33/58; G01N 33/582; G01N 33/532; C07D 495/22; C07D 209/18; C07D 493/14; C07D 311/18; C07D 401/10; C07D 209/14; C07D 311/82; C07F 5/022; C09B 45/00; C09B 11/26

See application file for complete search history.

(56) References Cited

U.S. PATENT DOCUMENTS

| | | | |
|---|---|---|---|
| 4,318,846 A | 3/1982 | Khanna et al. | |
| 4,384,042 A | 5/1983 | Miike et al. | |
| 4,420,568 A | 12/1983 | Wang et al. | |
| 4,510,251 A | 4/1985 | Kirkemo et al. | |
| 4,520,110 A | 5/1985 | Stryer et al. | |
| 4,542,104 A | 9/1985 | Stryer et al. | |
| 4,603,209 A | 7/1986 | Tsien et al. | |
| 4,711,955 A | 12/1987 | Ward et al. | |
| 4,774,339 A | 9/1988 | Haugland et al. | |
| 4,810,636 A | 3/1989 | Corey et al. | |
| 4,812,409 A | 3/1989 | Babb et al. | |
| 4,849,362 A | 7/1989 | Demarinis et al. | |
| 4,859,582 A | 8/1989 | Stryer et al. | |
| 4,945,171 A | 7/1990 | Haugland et al. | |
| 4,997,928 A | 3/1991 | Hobbs | |
| 5,047,519 A | 9/1991 | Hobbs et al. | |
| 5,049,673 A | 9/1991 | Tsien et al. | |
| 5,055,556 A | 10/1991 | Stryer et al. | |
| 5,132,432 A | 7/1992 | Haugland et al. | |
| 5,171,534 A | 12/1992 | Smith et al. | |
| 5,187,288 A | 2/1993 | Kang et al. | |
| 5,196,306 A | 3/1993 | Bobrow et al. | |
| 5,208,148 A | 5/1993 | Haugland et al. | |

(Continued)

FOREIGN PATENT DOCUMENTS

WO    WO-94/05688    3/1994

OTHER PUBLICATIONS

Hermanson, G.T., Bioconjugate Techniques 1996 Academic Press Ch. 1, p. 3-136 and Ch. 8, p. 297-416.*

(Continued)

*Primary Examiner* — Samantha Shterengarts
*Assistant Examiner* — Matt Mauro

(57) ABSTRACT

The present disclosure is directed to a reactive ester agent capable of conjugating a reporter molecule to a carrier molecule or solid support. The reactive ester agent has the general formula:

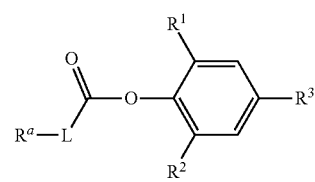

wherein the variables are described throughout the application.

17 Claims, 8 Drawing Sheets

(56) References Cited

U.S. PATENT DOCUMENTS

| | | |
|---|---|---|
| 5,227,487 A | 7/1993 | Haugland et al. |
| 5,242,805 A | 9/1993 | Naleway et al. |
| 5,248,782 A | 9/1993 | Haugland et al. |
| 5,268,486 A | 12/1993 | Waggoner et al. |
| 5,274,113 A | 12/1993 | Kang et al. |
| 5,316,906 A | 5/1994 | Haugland et al. |
| 5,332,666 A | 7/1994 | Prober |
| 5,362,628 A | 11/1994 | Haugland et al. |
| 5,405,975 A | 4/1995 | Kuhn et al. |
| 5,433,896 A | 7/1995 | Kang et al. |
| 5,442,045 A | 8/1995 | Haugland et al. |
| 5,443,986 A | 8/1995 | Haughland et al. |
| 5,451,343 A | 9/1995 | Neckers et al. |
| 5,453,517 A | 9/1995 | Kuhn et al. |
| 5,459,268 A | 10/1995 | Haugland et al. |
| 5,459,276 A | 10/1995 | Kuhn et al. |
| 5,486,616 A | 1/1996 | Waggoner et al. |
| 5,501,980 A | 3/1996 | Katerinopoulos et al. |
| 5,569,587 A | 10/1996 | Waggoner |
| 5,569,766 A | 10/1996 | Waggoner et al. |
| 5,576,424 A | 11/1996 | Mao et al. |
| 5,583,001 A | 12/1996 | Bobrow et al. |
| 5,627,027 A | 5/1997 | Waggoner |
| 5,648,270 A | 7/1997 | Kuhn et al. |
| 5,656,554 A | 8/1997 | Desai et al. |
| 5,686,261 A | 11/1997 | Zhang et al. |
| 5,696,157 A | 12/1997 | Wang et al. |
| 5,731,158 A | 3/1998 | Bobrow et al. |
| 5,773,236 A | 6/1998 | Diwu et al. |
| 5,798,276 A | 8/1998 | Haugland et al. |
| 5,800,996 A | 9/1998 | Lee et al. |
| 5,830,912 A | 11/1998 | Gee et al. |
| 5,846,737 A | 12/1998 | Kang |
| 5,847,162 A | 12/1998 | Lee et al. |
| 5,863,727 A | 1/1999 | Lee et al. |
| 5,945,526 A | 8/1999 | Lee et al. |
| 5,965,605 A | 10/1999 | Cheng et al. |
| 6,008,373 A | 12/1999 | Waggoner et al. |
| 6,008,379 A | 12/1999 | Benson et al. |
| 6,017,712 A | 1/2000 | Lee et al. |
| 6,025,505 A | 2/2000 | Lee et al. |
| 6,048,982 A | 4/2000 | Waggoner et al. |
| 6,080,852 A | 6/2000 | Lee et al. |
| 6,130,101 A | 10/2000 | Mao et al. |
| 6,140,494 A | 10/2000 | Hamilton et al. |
| 6,162,931 A | 12/2000 | Gee et al. |
| 6,184,379 B1 | 2/2001 | Josel et al. |
| 6,221,606 B1 | 4/2001 | Benson et al. |
| 6,229,055 B1 | 5/2001 | Klaubert et al. |
| 6,335,440 B1 | 1/2002 | Lee et al. |
| 6,339,392 B1 | 1/2002 | Ashihara et al. |
| 6,348,599 B1 | 2/2002 | Cummins et al. |
| 6,358,684 B1 | 3/2002 | Lee |
| 6,372,445 B1 | 4/2002 | Davis et al. |
| 6,403,807 B1 | 6/2002 | Singh et al. |
| 6,552,199 B1 | 4/2003 | Daltrozzo et al. |
| 6,562,632 B1 | 5/2003 | Szalecki et al. |
| 6,664,047 B1 | 12/2003 | Haugland et al. |
| 6,716,979 B2 | 4/2004 | Diwu et al. |
| 6,974,873 B2 | 12/2005 | Leung et al. |
| 6,977,305 B2 | 12/2005 | Leung et al. |
| 6,998,493 B2 | 2/2006 | Banning et al. |
| 7,026,166 B2 | 4/2006 | Suich et al. |
| 7,083,667 B2 | 8/2006 | Murai |
| 7,405,281 B2 | 7/2008 | Xu et al. |
| 8,143,069 B2 | 3/2012 | Nagano |
| 2009/0004753 A1 | 1/2009 | Antoulinakis et al. |

OTHER PUBLICATIONS

Hawley's Condensed Chemical Dictionary 2007 John Wiley & Sons, Inc., "Phosphor" accessed online Jul. 23, 2013 at: http://onlinelibrary.wiley.com/doi/10.1002/9780470114735.hawley12801/ful. I.*

Abrahart, E. , "Dyes and their Intermediates", 1969, pp. 8-9.

Beverloo, et al., "Immunochemical detection of proteins and nucleic acids on filters using small luminescent inorganic crystals as marker.", *Analytical Biochemistry*, 203, 1992, 326-34.

Bouizar, et al., "Purification and Characterization of Calcitonin Receptors in Rat Kidney Membranes by Covalent Cross-Linking Techniques.", *European Journal of Biochemistry*, vol. 155, No. 1, 1986, 141-147.

Brinkley, , "A Brief Survey of Methods for Preparing Protein Conjugates with Dyes, Haptens, and Cross-Linking Reagents", *Bioconjugate Chemistry*, vol. 3, No. 1, 1992, 2-13.

Browning, et al., "Studies on the Differing Effects of the Tumor Necrosis Factor and Lymphotoxin on the Growth of Several Human Tumor Lines", *Journal of Immunology*, vol. 143, No. 6, 1989, 1859-1867.

Gee, Kyle R. et al., "4-Sulfotetrafluorophenyl (STP) Esters: New Water-Soluble Amine-Reactive Reagents for Labeling Biomolecules", *Tetrahedron Letters*, vol. 40, 1999, 1471-1474.

Hedelberg, John F. et al., "The genome sequence of Vibrio cholerae, the etiologic agent of cholera.", *Nature*, vol. 406, Aug. 3, 2000, 477-483.

Helgason, Erlendur et al., "Bacillus anthracis, Bacillus cereus, and Bacillus thuringiensis—One Species on the Basis of Genetic Evidence.", *Appl. Envir. Microbiol.*, vol. 66, 2000, 2627-2630

Jiang, Sunny C. et al., "Genetic diversity of clinical and environmental isolates of Vibrio cholerae determined by amplified fragment length polymorphism (AFLP).", *Appl. Envir. Microbiol.*, 66, 2000, 148-153.

Joshi, et al., "ATP Synthase Complex from Bovine Heart Mitochondria", *Journal of Biological Chemistry*, vol. 265, No. 24, 1990, 14518-14525.

Jung, et al., "Crosslinking of platelet glycoprotein lb by N-succinimidyl(4-azidophenyldithio)propionate and 3,3'-dithiobis-(sulfosuccinimidyl propionate)", *Biochimica et Biophysica Acta*, vol. 761, No. 2, 1983, 152-162.

Kawasaki, Koichi et al., "A Water-Soluble Active Ester, Phenolsulfonic Acid Derivative", *Chemical & Pharmaceutical Bulletin*, vol. 35 (3). 1987, 1044-1048.

Park, et al., "Characterization of the Cell Surface Receptor for a Multi-Lineage Colony-Stimulating Factor (CSF-2alpha)*", *Journal of Biological Chemistry*, vol. 261, No. 1, 1986, 205-210.

Raju, B. et al., "A Fluorescent Indicator for Measuring Cytosolic Free Magnesium" *American Journal of Physiology, Laboratory of Molecular Biophysics*, National Institute of Environmental Health Sciences, 1989, C540-0548.

Tsuji, Toshiki et al., "Water-Soluble Active Ester. II. Esters of Phenolsulfonic Acid Derivatives", *Peptide Chemistry, 23rd*, 1986, 111-114.

Zarling, et al., "Mapping of Lymphocyte Surface Polypeptide Antigens by Chemical Cross-Linking with BSOCOES", *Journal of Immunology*, vol. 124, No. 2, 1980, 913-920.

\* cited by examiner

LABELING REAGENTS AND METHODS OF THEIR USE

CROSS-REFERENCE TO RELATED APPLICATIONS

This application is a Continuation application of U.S. application Ser. No. 13/972,081, filed Aug. 21, 2013, which is a Continuation of U.S. patent application Ser. No. 12/023,019, filed Jan. 30, 2008, now U.S. Pat. No. 8,586,743, which claims priority to U.S. Patent Application No. 60/887,218 filed Jan. 30, 2007, which disclosures is are herein incorporated by reference.

FIELD OF THE INVENTION

Novel compounds and methods of labeling are disclosed. The dyes are activated with water solublizing phenolic esters and contacted with a carrier molecule or solid support comprising a nucleophile to yield a stable conjugate comprising a dye labeled carrier molecule.

BACKGROUND OF THE INVENTION

The ability to effectively label a target molecule with a dye is highly dependent on the reactive groups present on each of the molecules in the reaction and the conjugation conditions. Reagents such as succinimidyl esters (SE) and perfluorophenyl (PFP) esters have high reactivity rates with water, thereby limiting preparation, packaging, dispensing and purification conditions and their subsequent shelf life. In addition, due to their hydrolytic reactivity, most of the reagents used for biomolecule labeling in aqueous buffers hydrolyze prior to reaction with the desired biomolecule and are therefore wasted.

Gee et al. (Tetrahedron Letters (1999), 40, 1471-1474) describes 4-sulfotetrafluorophenyl (STP) esters for use in dye labeling. These groups have been shown to be amenable to conjugation in aqueous environments.

Koichi et al. (Chemical & Pharmaceutical Bulletin (1987), 35(3), 1044-1048) and Tsuji et al. (Peptide Chemistry (1986), Volume Date 1985, 23rd 111-114) describe peptide synthesis via ester activation with potassium dichlorophenolsulfonate, sodium dibromophenolsulfonate, and sodium nitrophenolsulfonate. No description of labeling or conjugation of molecules such as dyes is provided.

While many labeling reagents exist and have been used with intermittent success, there remains a need for labeling reagents that produce high yields under biologically relevant reaction conditions. Additionally, a need exists for a conjugation product that is stable and does not hydrolyze in aqueous environments.

SUMMARY OF THE INVENTION

The present invention provides a reactive group, which has much greater hydrolytic stability than standard N-hydroxysuccinimidyl (SE) and perfluorophenolic (PFP) esters, and when attached to a reporter molecule forms a labeling reagent of the present invention. Additionally, the labeling reagent of the present invention is water soluble and yields a reporter molecule conjugate with exceptional stability.

One aspect of the present invention provides a compound of Formula IA or a tautomer or salt thereof:

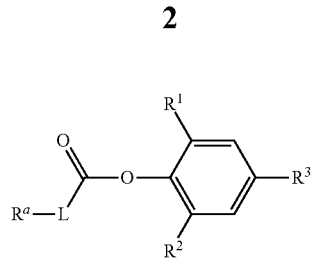

IA wherein,
L is a linker;
$R^1$ is a halogen;
$R^2$ is a halogen;
$R^3$ comprises a water solubilizing group; and
$R^a$ is a reporter molecule.

Another aspect of the invention provides a method of making a compound of Formula I comprising:
  contacting a carrier molecule or a solid support comprising a nucleophile with a compound of Formula IA or a tautomer or salt thereof:

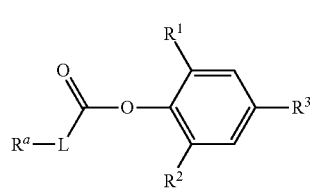

IA wherein,
L is a linker;
$R^1$ is a halogen;
$R^2$ is a halogen;
$R^3$ comprises a water solubilizing group; and
$R^a$ is a reporter molecule;
forming a compound of Formula I or a tautomer or salt thereof:

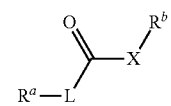

I wherein,
L is the linker;
$R^a$ is the reporter molecule; and
$R^b$ is the carrier molecule or solid support comprising a nucleophile (X).

Another aspect of the invention provides a method of labeling a carrier molecule or solid support comprising:
  contacting the carrier molecule or solid support with a compound of Formula IA or a tautomer or salt thereof:

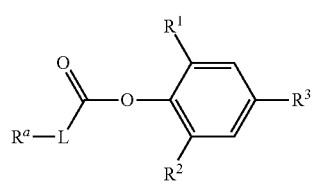

IA wherein,

L is a linker;

$R^1$ is a halogen;

$R^2$ is a halogen;

$R^3$ comprises a water solubilizing group;

$R^a$ is a reporter molecule; and the carrier molecule or solid support comprises a nucleophile; and forming a reporter molecule carrier molecule or solid support.

Another aspect of the invention provides a method of making a compound of Formula IA or a tautomer or salt thereof comprising:

contacting a compound of Formula IB or a tautomer or salt thereof:

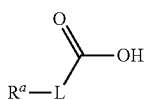

IB with a compound of Formula IC or a tautomer or salt thereof:

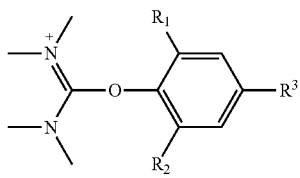

IC and forming the compound of Formula IA or a tautomer or salt thereof:

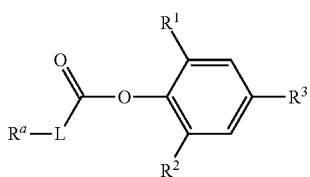

IA wherein, $R^1$ is a halogen;

$R^2$ is a halogen;

$R^3$ comprises a water solubilizing group;

L is a linker; and $R^a$ is a reporter molecule.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Introduction

Figure 1:
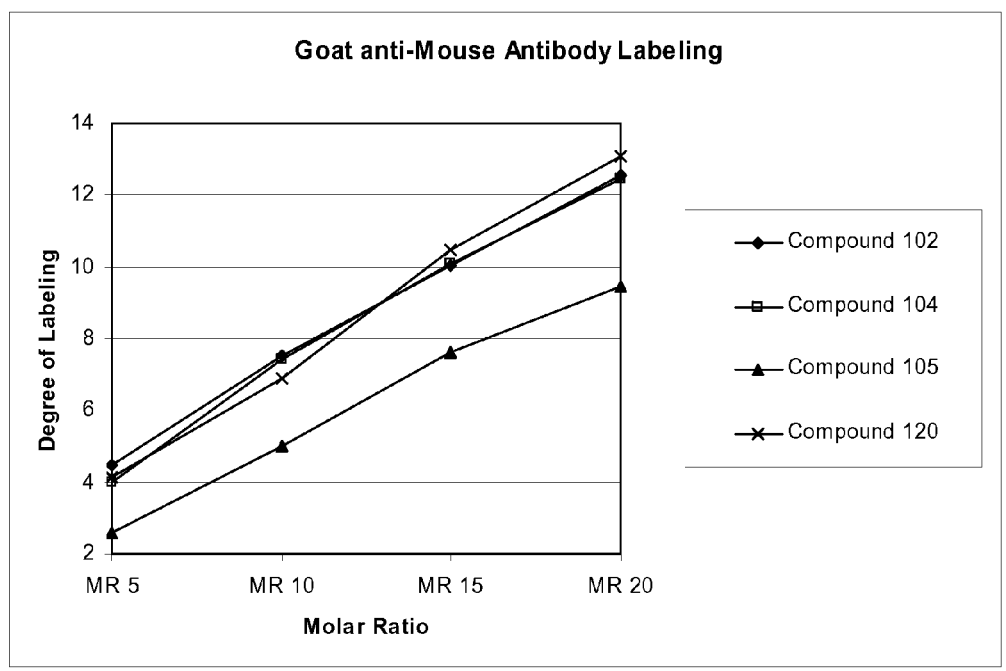
FIG. 1 shows goat anti-Mouse antibody labeling in 25 mM phosphate buffer pH 8.6 incubated for 1 hour at room temperature.
Figure 2:
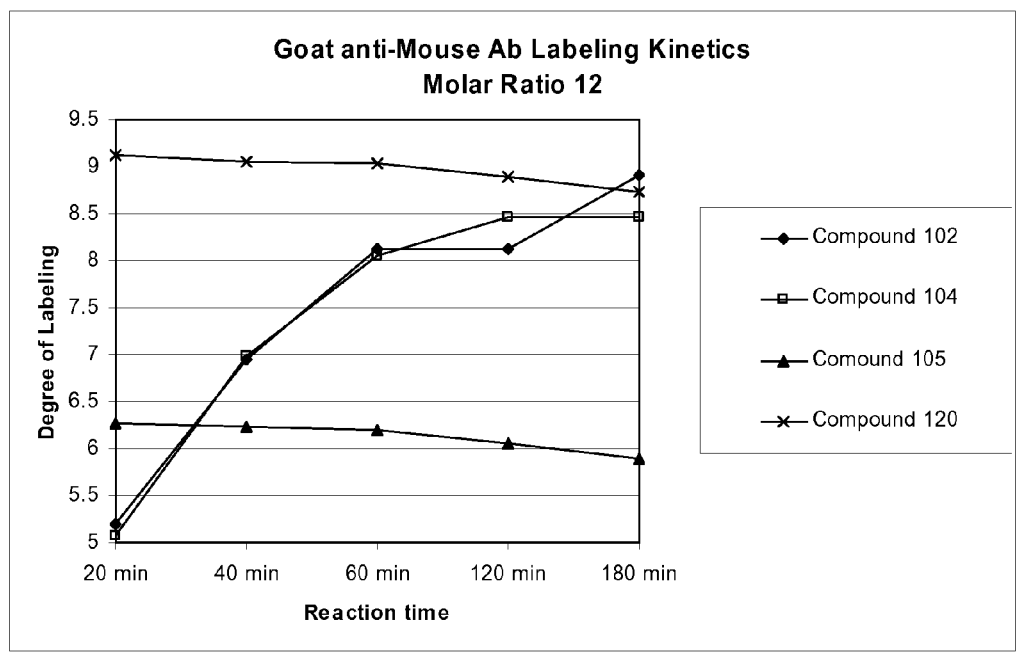
FIG. 2 shows goat anti-Mouse labeling kinetics in 25 mM phosphate buffer pH 8.6 incubated at room temperature with a molar ratio of 12.
Figure 3:
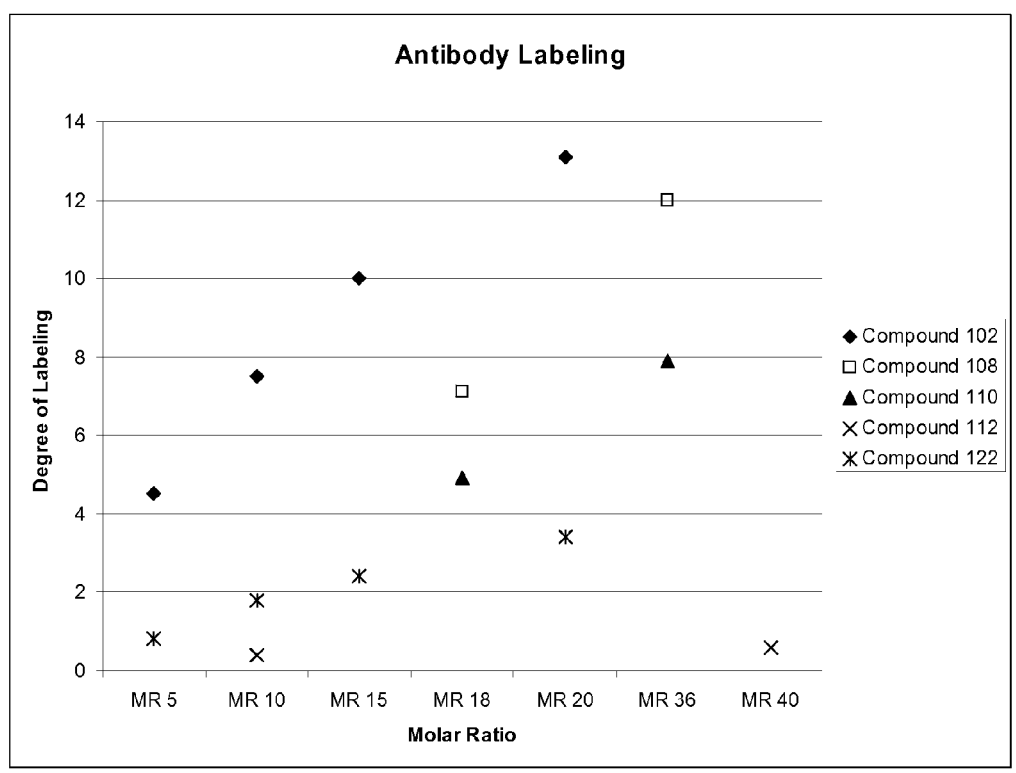
FIG. 3 shows goat anti-Mouse antibody labeling in 25 mM phosphate buffer pH 8.6 incubated at room temperature with the specified compound and molar ratio. The data shows that Compounds 112 and 122 which contain the dichlorophenol reactive ester react poorly with antibodies for labeling. In contrast, Compounds 102, 108 and 110 which contain the sulfodichlorophenol reactive ester are far superior for antibody labeling.
Figure 4:
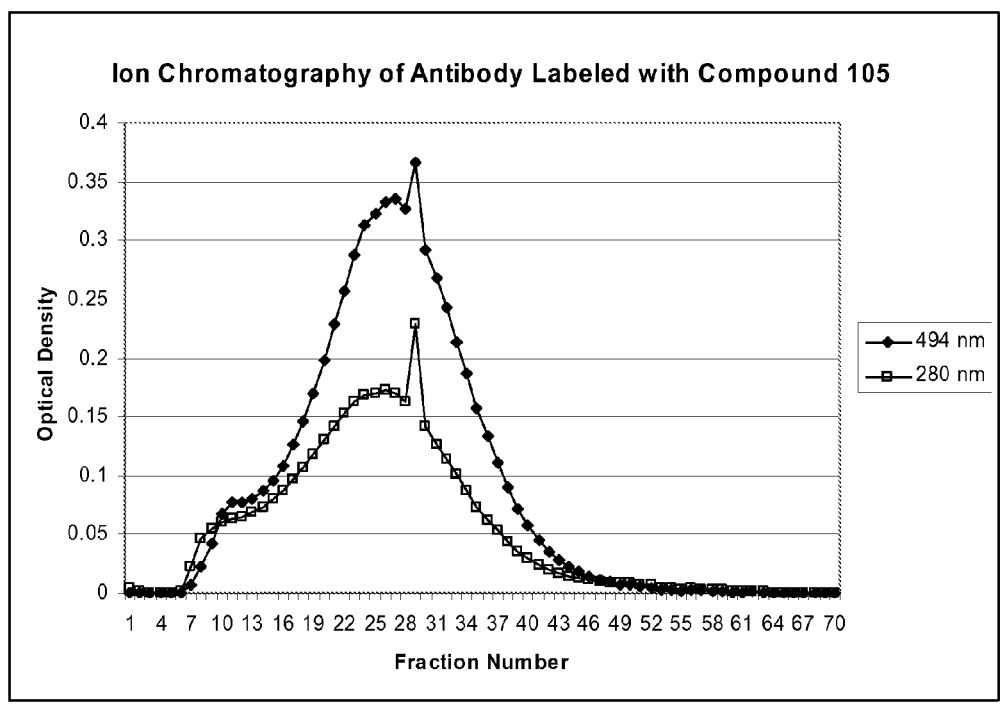
FIG. 4 shows ion chromatography with Macro-Prep DEAE Support (Bio-Rad) of Goat anti-Mouse antibody reporter molecule with compound 105, eluted with a 0-1.0 M NaCl gradient in 20 mM Tris pH 8. The chromatogram shows early fractions containing underlabeled antibody leading to a broadening of the peak. Under labeled antibodies can lead to decreased performance in labeling, detection and visualization activities.
Figure 5:
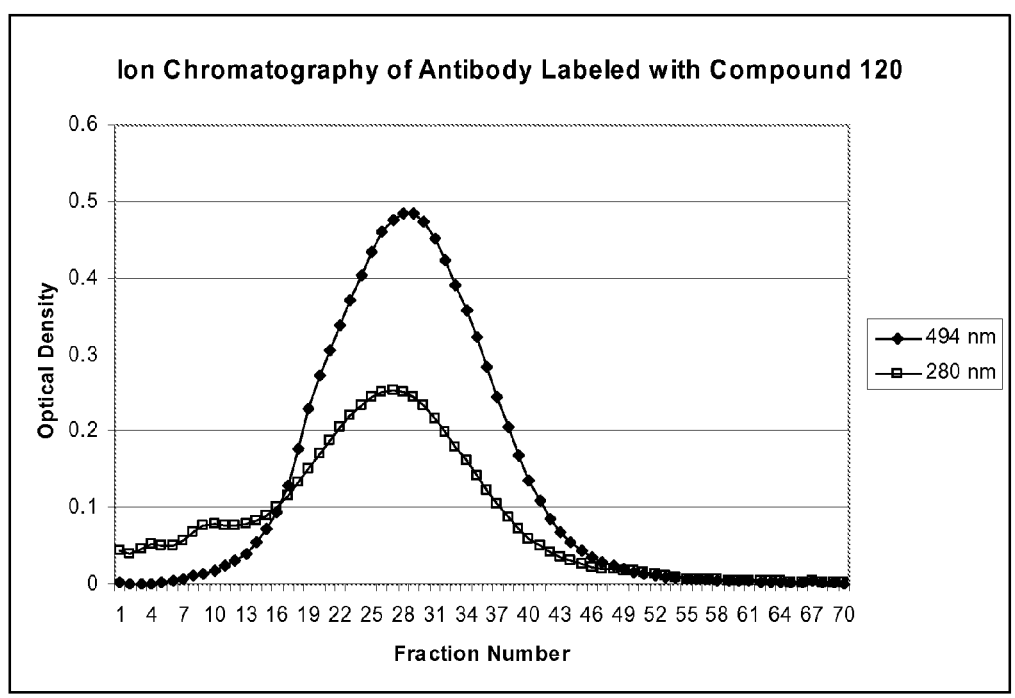
FIG. 5 shows ion chromatography with Macro-Prep DEAE Support (Bio-Rad) of Goat anti-Mouse antibody labeled with compound 120, eluted with a 0-1.0 M NaCl gradient in 20 mM Tris pH 8. The chromatogram shows early fractions containing unlabeled antibody and a broader peak of labeled antibody. Unlabeled antibodies can lead to decreased performance in labeling, detection and visualization activities.
Figure 6:
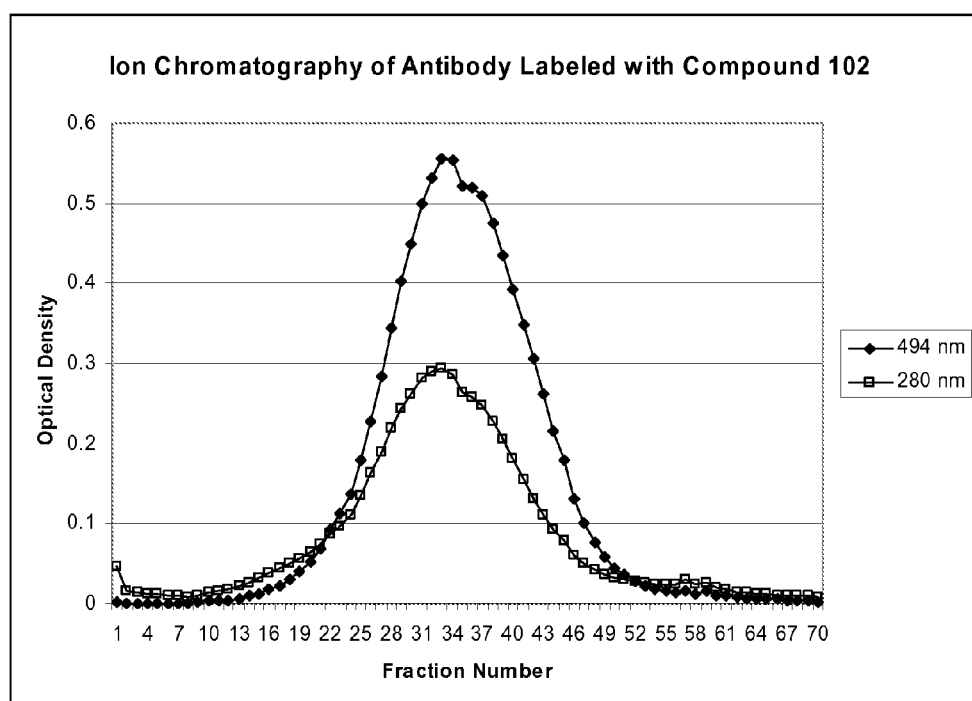
FIG. 6 shows ion chromatography with Macro-Prep DEAE Support (Bio-Rad) of Goat anti-Mouse antibody labeled with compound 102, eluted with a 0-1.0 M NaCl gradient in 20 mM Tris pH 8. The chromatogram shows a narrower peak of labeled antibody with almost no unlabeled or underlabeled peaks which can lead to better antibody performance in labeling, detection and visualization activities.
Figure 7:
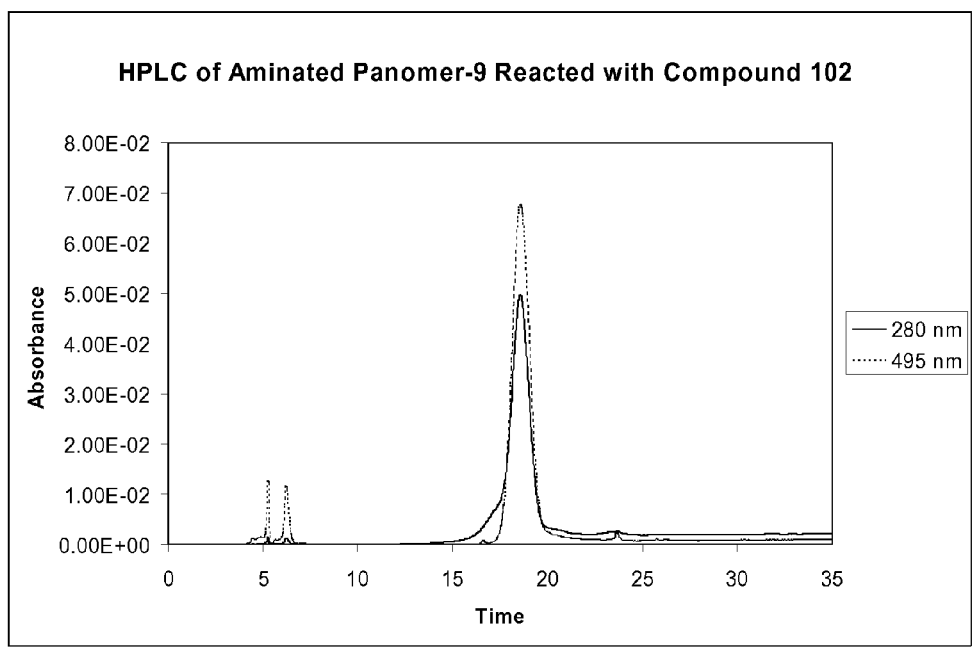
FIG. 7 shows HPLC (Phenomenex Luna C8 column; eluent: 20 mM TEAA pH 7, gradient 5-95% acetonitrile) trace of the crude reaction mixture of aminated Panomer-9 random oligonucleotides labeled with an 8-fold excess of compound 102 in borate buffer pH 8.5. The 280 nm trace detects the oligonucleotide while the 495 nm trace detects the dye reporter molecule. The chromatogram is very clean and shows only a few small reaction side products. The peak before the major peak in the 280 nm trace is unlabeled Panomer.
Figure 8:
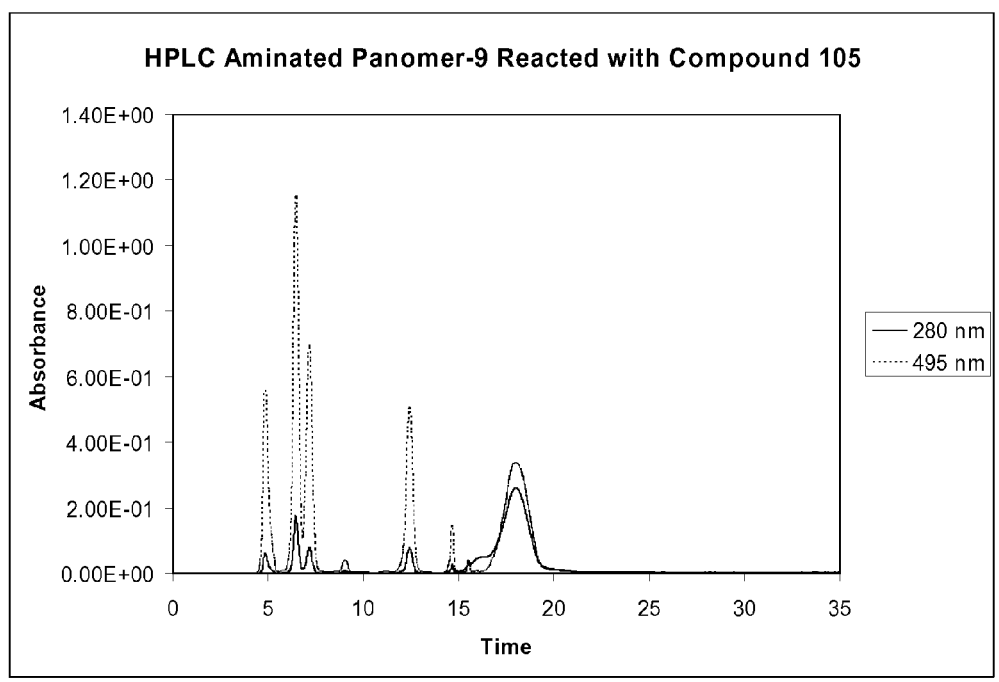
FIG. 8 shows HPLC (Phenomenex Luna C8 column; eluent: 20 mM TEAA pH 7, gradient 5-95% acetonitrile) trace of aminated Panomer-9 random oligonucleotides labeled with an 8-fold excess of compound 105 in borate buffer pH 8.5 and partially purified by repeated precipitations (4×) in ethanol. The 280 nm trace detects the oligonucleotide while the 495 nm trace detects the dye reporter molecule. The chromatogram shows larger amounts of multiple reaction side products. The peak before the major peak in the 280 nm trace is unlabeled Panomer.

The present invention provides labeling reagents for labeling carrier molecules or solid supports. The labeling reagents of the present invention generally include a compound of Formula IA, comprising an ester for activation of the reporter molecule. After activation, the reporter molecule is contacted with a carrier molecule or solid support comprising at least one nucleophile, such as an amine, thiol or hydroxyl group wherein a labeled conjugate is formed. The resultant compound is very stable, thereby providing an excellent method for labeling of a biomolecule such as a protein or polynucleotide. The resultant compound can subsequently be added to a biological solution for detection or monitoring purposes.

The esters described herein have excellent stability properties in aqueous solutions and retain a high degree of reactivity for amines on biomolecules, making them ideal choices for biomolecule labeling. The hydrolytic stability has significant impact on the preparation, ease of handling, storage stability, and biomolecule labeling efficiency. Additionally, by use of the labeling reagents of the present invention, purification of the molecule is significantly improved and can be done by silica gel flash chromatography. Column purification is not possible with many conventional SE or PFP esters, due to the high reactivity and low stability of the molecules. The esters of the present invention are also stable to lyophilization which greatly increases the ease of handling and packaging. With greater hydrolytic stability also come less degradation upon storage than existing ester modified dyes, such as SE and PFP.

In addition, with more hydrolytic stability comes greater labeling efficiency, with compounds of the present invention giving nearly twice as much biomolecule labeling as an equivalent amount of SE (see results in the Examples section).

Furthermore, the compounds of the present invention have been shown to be active to biomolecular labeling under a wide range of pH conditions, from pH 6-9. A wide pH reactivity range is a very important characteristic since many biomolecules are unable to be labeled at higher pH due to their limited solubility. This is also advantageous in the selective N-terminal labeling of proteins which generally occurs at a lower pH range.

DEFINITIONS

Before describing the present invention in detail, it is to be understood that this invention is not limited to specific compositions or process steps, as such may vary. It should be noted that, as used in this specification and the appended claims, the singular form "a", "an" and "the" include plural references unless the context clearly dictates otherwise. Thus, for example, reference to "a reporter molecule" includes a plurality of reporter molecules and reference to "an analyte" includes a plurality of analytes and the like.

Unless defined otherwise, all technical and scientific terms used herein have the same meaning as commonly understood by one of ordinary skill in the art to which this invention is related. The following terms are defined for purposes of the invention as described herein.

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

"Substituted alkyl" refers to an alkyl group having from 1 to 5, preferably 1 to 3, or more preferably 1 to 2 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined herein.

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Substituted alkoxy" refers to the group —O-(substituted alkyl) wherein substituted alkyl is defined herein.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein. Acyl includes the "acetyl" group $CH_3C(O)$—.

"Acylamino" refers to the groups —NRC(O)alkyl, —NRC(O)substituted alkyl, —NRC(O)cycloalkyl, —NRC(O)substituted cycloalkyl, —NRC(O)cycloalkenyl, —NRC(O)substituted cycloalkenyl, —NRC(O)alkenyl, —NRC(O)substituted alkenyl, —NRC(O)alkynyl, —NRC(O)substituted alkynyl, —NRC(O)aryl, —NRC(O)substituted aryl, —NRC(O)heteroaryl, —NRC(O)substituted heteroaryl, —NRC(O)heterocyclic, and —NRC(O)substituted heterocyclic wherein R is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, cycloalkenyl-C(O)O—, substituted cycloalkenyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Amino" refers to the group —NH$_2$.

"Substituted amino" refers to the group —NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic, —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-cycloalkenyl, —SO$_2$-substituted cycloalkenyl, —SO$_2$-aryl, —SO$_2$-substituted aryl, —SO$_2$— heteroaryl, —SO$_2$-substituted heteroaryl, —SO$_2$-heterocyclic, and —SO$_2$-substituted heterocyclic and wherein R' and R" are optionally joined, together with the nitrogen bound thereto to form a heterocyclic or substituted heterocyclic group, provided that R' and R" are both not hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. When R' is hydrogen and R" is alkyl, the substituted amino group is sometimes referred to herein as alkylamino. When R' and R" are alkyl, the substituted amino group is sometimes referred to herein as dialkylamino. When referring to a monosubstituted amino, it is meant that either R' or R" is hydrogen but not both. When referring to a disubstituted amino, it is meant that neither R' nor R" are hydrogen.

"Aminocarbonyl" refers to the group —C(O)NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminothiocarbonyl" refers to the group —C(S)N'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminocarbonylamino" refers to the group —NRC(O)NR'R" where R is hydrogen or alkyl and R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminothiocarbonylamino" refers to the group —NRC(S)N'R" where R is hydrogen or alkyl and R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminocarbonyloxy" refers to the group —O—C(O)NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminosulfonyl" refers to the group —SO$_2$NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminosulfonyloxy" refers to the group —O—SO$_2$N'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminosulfonylamino" refers to the group —NR—SO$_2$NR'R" where R is hydrogen or alkyl and R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkyenyl, heteroaryl, substituted heteroaryl, heterocyclic, and substituted heterocyclic and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkyenyl, aryl, substituted aryl, heteroaryl, substituted heteroaryl, heterocyclic and substituted heterocyclic are as defined herein.

"Amidino" refers to the group —C(=NR''')R'R" where R', R", and R''' are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is at an aromatic carbon atom. Preferred aryl groups include phenyl and naphthyl.

"Substituted aryl" refers to aryl groups which are substituted with 1 to 5, preferably 1 to 3, or more preferably 1 to 2 substituents selected from the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiol, alkylthio, and substituted alkylthio, wherein said substituents are defined herein.

"Aryloxy" refers to the group —O-aryl, where aryl is as defined herein, that includes, by way of example, phenoxy and naphthoxy.

"Substituted aryloxy" refers to the group —O-(substituted aryl) where substituted aryl is as defined herein.

"Arylthio" refers to the group —S-aryl, where aryl is as defined herein.

"Substituted arylthio" refers to the group —S-(substituted aryl), where substituted aryl is as defined herein.

"Alkenyl" refers to alkenyl groups having from 2 to 6 carbon atoms and preferably 2 to 4 carbon atoms and having at least 1 and preferably from 1 to 2 sites of alkenyl unsaturation. Such groups are exemplified, for example, by vinyl, allyl, and but-3-en-1-yl.

"Substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiol, alkylthio, and substituted alkylthio, wherein said substituents are defined herein and with the proviso that any hydroxy substitution is not attached to a vinyl (unsaturated) carbon atom.

"Alkynyl" refers to alkynyl groups having from 2 to 6 carbon atoms and preferably 2 to 3 carbon atoms and having at least 1 and preferably from 1 to 2 sites of alkynyl unsaturation.

"Substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiol, alkylthio, and substituted alkylthio, wherein said substituents are defined herein and with the proviso that any hydroxy substitution is not attached to an acetylenic carbon atom.

"Azenyl" refers to the group —N=NH. "Substituted azenyl" refers to —N=NR', wherein R' is alkyl, substituted alkyl, amino (i.e. triazenyl), imino (azide), substituted amino, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, or a substituted heterocyclic group.

"Carbonyl" refers to the divalent group —C(O)— which is equivalent to —C(=O)—.

"Carboxyl" or "carboxy" refers to —COOH or salts thereof.

"Carboxyl ester" or "carboxy ester" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)amino" refers to the group —NR—C(O)O-alkyl, substituted —NR—C(O)O-alkyl, —NR—C(O)O-alkenyl, —NR—C(O)O-substituted alkenyl, —NR—C(O)O-alkynyl, —NR—C(O)O-substituted alkynyl, —NR—C(O)O-aryl, —NR—C(O)O-substituted aryl, —NR—C(O)O-cycloalkyl, —NR—C(O)O-substituted cycloalkyl, —NR—C(O)O-cycloalkenyl, —NR—C(O)O-substituted cycloalkenyl, —NR—C(O)O-heteroaryl, —NR—C(O)O-substituted heteroaryl, —NR—C(O)O-heterocyclic, and —NR—C(O)O-substituted heterocyclic wherein R is alkyl or hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" refers to the group —O—C(O)O-alkyl, substituted —O—C(O)O-alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-cycloalkenyl, —O—C(O)O-substituted cycloalkenyl, —O—C(O)O-heteroaryl, —O—C(O)O-substituted heteroaryl, —O—C(O)O-heterocyclic, and —O—C(O)O-substituted heterocyclic wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" refers to the group —CN.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, and cyclooctyl.

"Cycloalkenyl" refers to non-aromatic cyclic alkyl groups of from 3 to 10 carbon atoms having single or multiple cyclic rings and having at least one >C=C< ring unsaturation and preferably from 1 to 2 sites of >C=C< ring unsaturation.

"Substituted cycloalkyl" and "substituted cycloalkenyl" refers to a cycloalkyl or cycloalkenyl group having from 1 to 5 or preferably 1 to 3 substituents selected from the group consisting of oxo, thione, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined herein.

"Cycloalkyloxy" refers to —O-cycloalkyl.

"Substituted cycloalkyloxy refers to —O-(substituted cycloalkyl).

"Cycloalkylthio" refers to —S-cycloalkyl.

"Substituted cycloalkylthio" refers to —S-(substituted cycloalkyl).

"Cycloalkenyloxy" refers to —O-cycloalkenyl.

"Substituted cycloalkenyloxy refers to —O-(substituted cycloalkenyl).

"Cycloalkenylthio" refers to —S-cycloalkenyl.

"Substituted cycloalkenylthio" refers to —S-(substituted cycloalkenyl).

"Guanidino" refers to the group —NHC(=NH)$NH_2$.

"Substituted guanidino" refers to —$NR^{13}C$(=$NR^{13}$)N($R^{13}$)$_2$ where each $R^{13}$ is independently selected from the group consisting of hydrogen, alkyl, substituted alkyl, aryl, substituted aryl, heteroaryl, substituted heteroaryl, heterocyclic, and substituted heterocyclic and two $R^{13}$ groups attached to a common guanidino nitrogen atom are optionally joined together with the nitrogen bound thereto to form a heterocyclic or substituted heterocyclic group, provided that at least one $R^{13}$ is not hydrogen, and wherein said substituents are as defined herein.

"H" indicates hydrogen.

"Halo" or "halogen" refers to fluoro, chloro, bromo and iodo.

"Hydroxy" or "hydroxyl" refers to the group —OH.

"Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N-oxide (N→O), sulfinyl, or sulfonyl moieties. Preferred heteroaryls include pyridinyl, pyrrolyl, indolyl, thiophenyl, and furanyl.

"Substituted heteroaryl" refers to heteroaryl groups that are substituted with from 1 to 5, preferably 1 to 3, or more preferably 1 to 2 substituents selected from the group consisting of the same group of substituents defined for substituted aryl.

"Heteroaryloxy" refers to —O-heteroaryl.

"Substituted heteroaryloxy refers to the group —O-(substituted heteroaryl).

"Heteroarylthio" refers to the group —S-heteroaryl.

"Substituted heteroarylthio" refers to the group —S-(substituted heteroaryl).

"Heterocycle" or "heterocyclic" or "heterocycloalkyl" or "heterocyclyl" refers to a saturated or unsaturated group having a single ring or multiple condensed rings, including fused bridged and spiro ring systems, from 1 to 10 carbon atoms and from 1 to 4 hetero atoms selected from the group consisting of nitrogen, sulfur or oxygen within the ring wherein, in fused ring systems, one or more the rings can be cycloalkyl, aryl or heteroaryl provided that the point of attachment is through the non-aromatic ring. In one embodiment, the nitrogen and/or sulfur atom(s) of the heterocyclic group are optionally oxidized to provide for the N-oxide, sulfinyl, sulfonyl moieties.

"Substituted heterocyclic" or "substituted heterocycloalkyl" or "substituted heterocyclyl" refers to heterocyclyl groups that are substituted with from 1 to 5 or preferably 1 to 3 of the same substituents as defined for substituted cycloalkyl.

"Heterocyclyloxy" refers to the group —O-heterocycyl.

"Substituted heterocyclyloxy refers to the group —O-(substituted heterocycyl).

"Heterocyclylthio" refers to the group —S-heterocycyl.

"Substituted heterocyclylthio" refers to the group —S-(substituted heterocycyl).

Examples of heterocycle and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, and tetrahydrofuranyl.

"Hydrazinyl" refers to the group —NHNH$_2$—, =NNH—, or =N$^{(+)}$HNH$_2$—.

"Substituted hydrazinyl" refers to a hydrazinyl group, wherein a non-hydrogen atom, such as an alkyl group, is appended to one or both of the hydrazinyl amine groups. An example of substituted hydrazinyl is —N(alkyl)-NH$_2$ or =N$^+$(alkyl)-NH$_2$.

"Nitro" refers to the group —NO$_2$.

"Oxo" refers to the atom (=O) or (—O$^-$).

"Spirocyclyl" refers to divalent saturated cyclic group from 3 to 10 carbon atoms having a cycloalkyl or heterocyclyl ring with a Spiro union (the union formed by a single atom which is the only common member of the rings) as exemplified by the following structure:

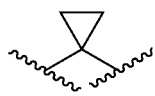

"Sulfonyl" refers to the divalent group —S(O)$_2$—.

"Substituted sulfonyl" refers to the group —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-cycloalkenyl, —SO$_2$-substituted cycloalkenyl, —SO$_2$-aryl, —SO$_2$-substituted aryl, —SO$_2$-heteroaryl, —SO$_2$— substituted heteroaryl, —SO$_2$-heterocyclic, —SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein. Substituted sulfonyl includes groups such as methyl-SO$_2$—, phenyl-SO$_2$—, and 4-methylphenyl-SO$_2$—.

"Sulfonyloxy" refers to the group —OSO$_2$-alkyl, —OSO$_2$-substituted alkyl, —OSO$_2$-alkenyl, —OSO$_2$-substituted alkenyl, —OSO$_2$-cycloalkyl, —OSO$_2$-substituted cycloalkyl, —OSO$_2$-cycloalkenyl, —OSO$_2$-substituted cycloalkenyl, —OSO$_2$-aryl, —OSO$_2$-substituted aryl, —OSO$_2$— heteroaryl, —OSO$_2$-substituted heteroaryl, —OSO$_2$-heterocyclic, —OSO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Thioacyl" refers to the groups H—C(S)—, alkyl-C(S)—, substituted alkyl-C(S)—, alkenyl-C(S)—, substituted alkenyl-C(S)—, alkynyl-C(S)—, substituted alkynyl-C(S)—, cycloalkyl-C(S)—, substituted cycloalkyl-C(S)—, cycloalkenyl-C(S)—, substituted cycloalkenyl-C(S)—, aryl-C(S)—, substituted aryl-C(S)—, heteroaryl-C(S)—, substituted heteroaryl-C(S)—, heterocyclic-C(S)—, and substituted heterocyclic-C(S)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Thiol" refers to the group —SH.

"Thiocarbonyl" refers to the divalent group —C(S)— which is equivalent to —C(=S)—.

"Thione" refers to the atom (=S).

"Alkylthio" refers to the group —S-alkyl wherein alkyl is as defined herein.

"Substituted alkylthio" refers to the group —S-(substituted alkyl) wherein substituted alkyl is as defined herein.

A squiggly line intersecting a bond, such as:

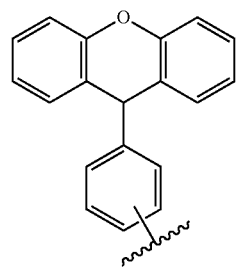

indicates the point of attachment to the base molecule, wherein in the above structure the point of attachment is any unoccupied position on the phenyl ring.

"Stereoisomer" or "stereoisomers" refer to compounds that differ in the chirality of one or more stereocenters. Stereoisomers include enantiomers and diastereomers.

"Tautomer" refers to alternate forms of a compound that differ in the position of a proton, such as enol-keto and imine-enamine tautomers, or the tautomeric forms of heteroaryl groups containing a ring atom attached to both a ring —NH— moiety and a ring =N— moeity such as pyrazoles, imidazoles, benzimidazoles, triazoles, and tetrazoles.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group etc.) are not intended for inclusion herein. In such cases, the maximum number of such substitutions is three. For example, serial substitutions of substituted aryl groups with two other substituted aryl groups are limited to -substituted aryl-(substituted aryl)-substituted aryl.

Similarly, it is understood that the above definitions are not intended to include impermissible substitution patterns (e.g., methyl substituted with 5 fluoro groups). Such impermissible substitution patterns are well known to the skilled artisan.

"Salt" refers to acceptable salts of a compound, which salts are derived from a variety of organic and inorganic counter ions well known in the art and include, by way of example only, sodium, potassium, calcium, magnesium, ammonium, and tetraalkylammonium; and when the molecule contains a basic functionality, salts of organic or inorganic acids, such as hydrochloride, hydrobromide, tartrate, mesylate, acetate, maleate, and oxalate.

The terms "protein" and "polypeptide" are used herein in a generic sense to include polymers of amino acid residues of any length. The term "peptide" is used herein to refer to polypeptides having less than 250 amino acid residues, typically less than 100 amino acid residues. The terms apply to amino acid polymers in which one or more amino acid residues are an artificial chemical analogue of a corresponding naturally occurring amino acid, as well as to naturally occurring amino acid polymers.

A "water solubilizing group" as used herein indicates a polar and/or charged, preferably anionic, substituent that increases water solubility of a base molecule. Water solubilizing groups may be appended directly to the base molecule, or through a linker. Water solubilizing groups of the present invention include carboxyl groups, sulphonic acids, hydroxyl groups, substituted azenyl groups, polyoxyalkylene (such as PEG), phosphate groups, bisphosphonate groups, or substitutions that introduce an additional net charge and/or polarity into the molecule.

The term "reactive group" as used herein refers to a group that is capable of reacting with another chemical group to form a covalent bond, i.e. is covalently reactive under suitable reaction conditions, and generally represents a point of attachment for another substance. In the present invention the labeling reagents comprise a reactive group according to Formula IA and the carrier molecule or solid support comprises at least one suitable nucleophile that will react with the reactive group according to Formula IA to form a covalent bond.

The term "detectable response" as used herein refers to an occurrence of or a change in, a signal that is directly or indirectly detectable either by observation or by instrumentation. Typically, the detectable response is an optical response resulting in a change in the wavelength distribution patterns or intensity of absorbance or fluorescence or a change in light scatter, fluorescence lifetime, fluorescence polarization, or a combination of the above parameters.

The term "dye" as used herein refers to a compound that emits light to produce an observable detectable signal.

The term "fluorophore" or "fluorogenic" as used herein refers to a composition that demonstrates a change in fluorescence upon binding to a biological compound or analyte interest. Preferred fluorophores of the present invention include fluorescent dyes having a high quantum yield in aqueous media. Exemplary fluorophores include xanthene, indole, borapolyazaindacene, furan, and benzofuran, among others. The fluorophores of the present invention may be substituted to alter the solubility, spectral properties or physical properties of the fluorophore.

The term "carrier molecule" as used herein refers to a biological or a non-biological component that can be covalently bonded to a labeling reagent of the present invention. Such components include, but are not limited to, an amino acid, a peptide, a protein, a polysaccharide, a nucleoside, a nucleotide, an oligonucleotide, a nucleic acid, a hapten, a psoralen, a drug, a hormone, a lipid, a lipid assembly, a synthetic polymer, a polymeric microparticle, a biological cell, a virus and combinations thereof. As used herein carrier molecules comprise a nucleophile for reaction with the present labeling reagents. Carrier molecules are described in greater detail below.

"Covalently bonded" as used herein indicates a direct covalent linkage or through a number of atoms corresponding to a linker moiety.

The term "reporter molecule" as used herein refers to a chemical moiety or protein that retains it's native properties (e.g. spectral properties, conformation and activity) when part of a labeling reagent of the present invention and used in the present methods. Illustrative reporter molecules can be directly detectable (fluorophore) or indirectly detectable (hapten or enzyme). Such reporter molecules include, but are not limited to, radio reporter molecules that can be measured with radiation-counting devices; pigments, dyes or other chromogens that can be visually observed or measured with a spectrophotometer; spin labels that can be measured with a spin label analyzer; and fluorescent moieties, where the output signal is generated by the excitation of a suitable molecular adduct and that can be visualized by excitation with light that is absorbed by the dye or can be measured with standard fluorometers or imaging systems, for example. The reporter molecule can be a luminescent substance such as a phosphor or fluorogen; a bioluminescent substance; a chemiluminescent substance, where the output signal is generated by chemical modification of the signal compound; a metal-containing substance; or an enzyme, where there occurs an enzyme-dependent secondary generation of signal, such as the formation of a colored product from a colorless substrate. The reporter molecule may also take the form of a chemical or biochemical, or an inert particle, including but not limited to colloidal gold, microspheres, quantum dots, or inorganic crystals such as nanocrystals or phosphors (see, e.g., Beverloo, et al., Anal. Biochem. 203, 326-34 (1992)). The term reporter molecule can also refer to a "tag" or hapten that can bind selectively to a labeled molecule such that the labeled molecule, when added subsequently, is used to generate a detectable signal. For instance, one can use biotin, iminobiotin or desthiobiotin as a tag and then use an avidin or streptavidin conjugate of horseradish peroxidase (HRP) to bind to the tag, and then use a chromogenic substrate (e.g., tetramethylbenzidine) or a fluorogenic substrate such as Amplex Red or Amplex Gold (Molecular Probes, Inc.) to detect the presence of HRP. In a similar fashion, the tag can be a hapten or antigen (e.g., digoxigenin), and an enzymatically, fluorescently, or radioactively labeled antibody can be used to bind to the tag. Numerous reporter molecules are known by those of skill in the art and include, but are not limited to, particles, fluorescent dyes, haptens, enzymes and their chromogenic, fluorogenic, and chemiluminescent substrates, and other reporter molecules that are described in the MOLECULAR PROBES HANDBOOK OF FLUORESCENT PROBES AND RESEARCH CHEMICALS by Richard P. Haugland, $10^{th}$ Ed., (2005), the contents of which are incorporated by reference, and in other published sources. As used herein a reporter molecule is not an amino acid.

The term "Labeling Reagent" as used herein refers to present compound that comprises a reporter molecule and a reactive group according to Formula IA.

The term "Linker" as used herein, refers to a single covalent bond or a series of stable covalent bonds incorporating 1-20 nonhydrogen atoms selected from the group consisting of C, N, O, S and P. The present labeling reagent may comprise a linker that covalently attaches the reporter molecule to the reactive group according to Formula IA or to a carrier group or solid support. Exemplary linking members include a moiety that includes —C(O)NH—, —C(O)O—, —NH—, —S—, —O—, and the like. A "cleavable linker" is a linker that has one or more cleavable groups that may be broken by the result of a reaction or condition. The term "cleavable group" refers to a moiety that allows for release of a portion, e.g., a fluorogenic or fluorescent moiety, of a conjugate from the remainder of the conjugate by cleaving a bond linking the released moiety to the remainder of the conjugate. Such cleavage is either chemical in nature, or enzymatically mediated. Exemplary enzymatically cleavable groups include natural amino acids or peptide sequences that end with a natural amino acid.

In addition to enzymatically cleavable groups, it is within the scope of the present invention to include one or more sites that are cleaved by the action of an agent other than an enzyme. Exemplary non-enzymatic cleavage agents include, but are not limited to, acids, bases, light (e.g., nitrobenzyl derivatives, phenacyl groups, benzoin esters), and heat. Many cleaveable groups are known in the art. See, for example, Jung et al., *Biochem. Biophys. Acta*, 761: 152-162 (1983); Joshi et al., *J. Biol. Chem.*, 265: 14518-14525 (1990); Zarling et al., *J. Immunol.*, 124: 913-920 (1980); Bouizar et al., *Eur. J. Biochem.*, 155: 141-147 (1986); Park et al., *J. Biol. Chem.*, 261: 205-210 (1986); Browning et al., *J. Immunol.*, 143: 1859-1867 (1989). Moreover a broad range of cleavable, bifunctional (both homo- and heterobifunctional) spacer arms are commercially available.

An exemplary cleavable group, an ester, is cleavable group that may be cleaved by a reagent, e.g. sodium hydroxide, resulting in a carboxylate-containing fragment and a hydroxyl-containing product.

The term "sample" as used herein refers to any material that may contain an analyte of interest, as defined below, or a carrier molecule or solid support of the present invention. Typically, the sample comprises a population of cells, cellular extract, subcellular components, tissue culture, a bodily fluid, and tissue. The sample may be in an aqueous solution, a viable cell culture or immobilized on a solid or semi solid surface such as a gel, a membrane, a glass surface, a microparticle or on a microarray.

The term "solid support" as used here refers to a matrix or media that is substantially insoluble in liquid phases and capable of binding a molecule or particle of interest. Solid supports of the current invention include semi-solid supports and are not limited to a specific type of support. Useful solid supports include solid and semi-solid matrixes, such as aerogels and hydrogels, resins, beads, biochips (including thin film coated biochips), microfluidic chip, a silicon chip, multi-well plates (also referred to as microtitre plates or microplates), membranes, conducting and nonconducting metals, glass (including microscope slides) and magnetic supports. More specific examples of useful solid supports include silica gels, polymeric membranes, particles, derivatized plastic films, glass beads, cotton, plastic beads, alumina gels, polysaccharides such as Sepharose, poly(acrylate), polystyrene, poly(acrylamide), polyol, agarose, agar, cellulose, dextran, starch, FICOLL, heparin, glycogen, amylopectin, mannan, inulin, nitrocellulose, diazocellulose, polyvinylchloride, polypropylene, polyethylene (including poly(ethylene glycol)), nylon, latex bead, magnetic bead, paramagnetic bead, superparamagnetic bead, starch and the like.

The Labeling Reagents

In accordance with the present invention, labeling reagents, methods for labeling carrier molecules or solid support and methods for using the labeled conjugates to detect an analyte of interest in a sample are provided. The labeling reagents comprise a reporter molecule, as defined herein, and a reactive group according to Formula IA, as defined below. The labeling reagents are then used to label a wide range of carrier molecules and solid supports by methods well known in the art and used in a wide range of assays and applications for the detection of a particular analyte.

Labeling Reagents

One aspect of the present invention provides a compound of Formula IA or a tautomer or salt thereof:

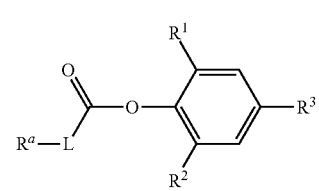

IA wherein,
L is a linker;
$R^1$ is a halogen;
$R^2$ is a halogen;
$R^3$ comprises a water solubilizing group; and
$R^a$ is a reporter molecule.

In another more particular embodiment, L is a covalent bond, -alkyl-, -substituted alkyl-, -alkenyl-, -substituted alkenyl-, -heterocyclyl-, -substituted heterocyclyl-, -aryl-, -substituted aryl-, -heteroaryl-, -substituted heteroaryl-, -cycloakyl-, -substituted cycloalkyl-, -oxy-, -alkoxy-, -substituted alkoxy-, -thio-, -amino-, or -substituted amino-. More particular still, L is single a covalent bond. Alternatively, L is -alkyl- or -substituted alkyl-; more particularly -pentyl- or -polyethylglycol- or -amino-dPEG$_4$-acid. Alternatively, L is -substituted heterocyclyl-; more particularly, -piperidine-1-carbonyl-.

In another embodiment, $R^1$ and $R^2$ are chloro. In an alternative another embodiment $R^1$ and $R^2$ are fluoro.

In another embodiment, $R^3$ is —COO$^-$, —SO$_3^-$, substituted azenyl, PEG, phosphate, or bisphosphonate. More particularly, $R^3$ is —SO$_3^-$.

In another embodiment, $R^a$ is a dye. More particularly, the dye is a xanthene, a cyanine, an indole, a benzofuran, a coumarin, or a borapolyazaindacine.

In another embodiment, $R^a$ is a chelating moiety, a hapten, an antibody, an enzyme, a radiolabel, a metal ion or a particle comprising a metal ion, a pigment, a chromogen, a phosphor, a fluorogen, a bioluminescent substance, a chemiluminescent substance, or a semiconductor nanocrystal. More particularly, $R^a$ is avidin, streptavidin or an analog thereof.

In another embodiment, the compound of Formula IA is a salt. More particularly, the salt comprises a potassium or sodium ion.

In another embodiment, the reporter molecule is hydrophobic. In another embodiment, the compound of Formula IA is soluble in an aqueous solution.

In another embodiment, the compound has a Formula IAA:

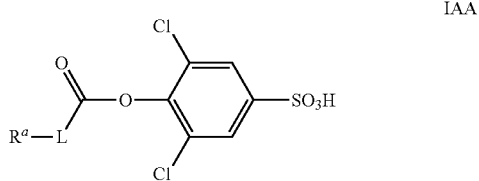

IAA or a tautomer or stereoisomer thereof,
wherein,
$R^a$ is a reporter molecule.

In another embodiment, the present compound has a Formula XXX

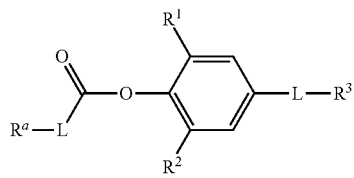

wherein the variables are as described herein, and each L group is independent of the other.

Reporter Molecules

The reporter molecules of the present invention functions as a reporter moiety to confer a detectable signal, directly or indirectly, to the conjugated carrier molecule, solid support or analyte, directly or indirectly, in a sample. This conjugated labeling reagent results in the ability to detect, monitor, isolate, sequester, and quantitate a carrier molecule, a solid support or an analyte in a sample.

The present reporter molecules can be any reporter molecule known to one skilled in the art. A wide variety of fluorescent dyes with appropriate reactivity may be suitable for incorporation into the compounds of the invention are already known in the art (MOLECULAR PROBES HANDBOOK OF FLUORESCENT PROBES AND RESEARCH CHEMICALS by Richard P. Haugland, 10$^{th}$ Ed., (2005)). Reporter molecules include, without limitation, a fluorophore, a fluorescent protein, a tandem dye (energy transfer pair), a ion chelating moiety, a radio label, spin labels, luminescent label, enzyme, hapten, colloid gold, quantum dot, nanocrystals, microspheres, or a fluorogenic enzyme substrate.

A fluorescent dye of the present invention is any chemical moiety that exhibits an absorption maximum beyond 280 nm, and when covalently linked to the ester moiety moiety of the present invention, forms a present labeling reagent.

Dyes of the present invention include, without limitation; a pyrene, an anthracene, a naphthalene, an acridine, a stilbene, an indole or benzindole, an oxazole or benzoxazole, a thiazole or benzothiazole, a 4-amino-7-nitrobenz-2-oxa-1, 3-diazole (NBD), a carbocyanine (including any corresponding compounds in U.S. Pat. Nos. 6,664,047; 6,977,305; 6,974,873; 6,403,807; 6,348,599; 5,486,616; 5,268,486; 5,569,587; 5,569,766; 5,627,027 and 6,048,982), a carbostyryl, a porphyrin, a salicylate, an anthranilate, an azulene, a perylene, a pyridine, a quinoline, a borapolyazaindacene (including any corresponding compounds disclosed in U.S. Pat. Nos. 4,774,339; 5,187,288; 5,248,782; 5,274,113; and 5,433,896), a xanthene (including any corresponding compounds disclosed in U.S. Pat. Nos. 6,162,931; 6,130,101; 6,229,055; 6,339,392; 5,451,343 and 6,716,979), an oxazine or a benzoxazine, a carbazine (including any corresponding compounds disclosed in U.S. Pat. No. 4,810,636), a phenalenone, a coumarin (including an corresponding compounds disclosed in U.S. Pat. Nos. 5,696,157; 5,459,276; 5,501,980 and 5,830,912), a benzofuran (including an corresponding compounds disclosed in U.S. Pat. Nos. 4,603,209 and 4,849,362) and benzphenalenone (including any corresponding compounds disclosed in U.S. Pat. No. 4,812,409) and derivatives thereof. As used herein, oxazines include resorufins (including any corresponding compounds disclosed in U.S. Pat. No. 5,242,805), aminooxazinones, diaminooxazines, and their benzo-substituted analogs.

Where the dye is a xanthene, the dye is optionally a fluorescein, a rhodol (including any corresponding compounds disclosed in U.S. Pat. Nos. 5,227,487 and 5,442,045), a rosamine or a rhodamine (including any corresponding compounds in U.S. Pat. Nos. 5,798,276; 5,846,737; 5,847,162; 6,017,712; 6,025,505; 6,080,852; 6,716,979; 6,562,632). As used herein, fluorescein includes benzo- or dibenzofluoresceins, seminaphthofluoresceins, or naphthofluoresceins. Similarly, as used herein rhodol includes seminaphthorhodafluors (including any corresponding compounds disclosed in U.S. Pat. No. 4,945,171). Fluorinated xanthene dyes have been described previously as possessing particularly useful fluorescence properties (U.S. Pat. No. 6,162,931).

Preferred dyes of the invention include dansyl, xanthene, cyanine, borapolyazaindacene, pyrene, naphthalene, coumarin, oxazine and derivatives thereof. Preferred xanthenes are fluorescein, rhodamine and derivatives thereof, naphthalene and dansyl.

Typically the dye contains one or more aromatic or heteroaromatic rings, that are optionally substituted one or more times by a variety of substituents, including without limitation, halogen, nitro, sulfo, cyano, alkyl, perfluoroalkyl, alkoxy, alkenyl, alkynyl, cycloalkyl, arylalkyl, acyl, aryl or heteroaryl ring system, benzo, or other substituents typically present on chromophores or fluorophores known in the art.

In an exemplary embodiment, the dyes are independently substituted by substituents selected from the group consisting of hydrogen, halogen, amino, substituted amino, alkyl, substituted alkyl, aryl, substituted aryl, heteroaryl, substituted heteroaryl, alkoxy, sulfo, reactive group and carrier molecule. In another embodiment, the xanthene dyes of this invention comprise both compounds substituted and unsubstituted on the carbon atom of the central ring of the xanthene by substituents typically found in the xanthene-based dyes such as phenyl and substituted-phenyl moieties. Most preferred dyes are rhodamine, fluorescein, dansyl, naphthalene and derivatives thereof. The choice of the dye attached to the chelating moiety will determine the metal ion-binding compound's absorption and fluorescence emission properties as well as its live cell properties, i.e. ability to localize to mitochondria.

Selected sulfonated reporter molecules also exhibit advantageous properties, and include sulfonated pyrenes, coumarins, carbocyanines, and xanthenes (as described in U.S. Pat. Nos. 5,132,432; 5,696,157; 5,268,486; 6,130,101). Sulfonated pyrenes and coumarins are typically excited at wavelengths below about 450 nm (U.S. Pat. Nos. 5,132,432 and 5,696,157).

Fluorescent proteins also find use as reporter moieties for the chelate compounds of the present invention. Examples of fluorescent proteins include green fluorescent protein (GFP) and the phycobiliproteins and the derivatives thereof. The fluorescent proteins, especially phycobiliproteins, are particularly useful for creating tandem dye-reporter molecules. These tandem dyes comprise a fluorescent protein and a fluorophore for the purposes of obtaining a larger Stokes shift, wherein the emission spectra are farther shifted from the wavelength of the fluorescent protein's absorption spectra. This property is particularly advantageous for detecting a low quantity of a target ion in a sample wherein the emitted fluorescent light is maximally optimized; in other words, little to none of the emitted light is reabsorbed by the fluorescent protein. For this to work, the fluorescent protein and fluorophore function as an energy transfer pair wherein the fluorescent protein emits at the wavelength that the acceptor fluorophore absorbs and the fluorophore then emits at a wavelength farther from the fluorescent proteins than could have been obtained with only the fluorescent protein. Alternatively, the fluorophore functions as the energy donor and the fluorescent protein is the energy acceptor. Particularly useful fluorescent proteins are the phycobiliproteins disclosed in U.S. Pat. Nos. 4,520,110; 4,859,582; 5,055,556 and the fluorophore bilin protein combinations disclosed in U.S. Pat. No. 4,542,104. Alternatively, two or more fluorophore dyes can function as an energy transfer pair wherein one fluorophore is a donor dye and the other is the acceptor dye including any dye compounds disclosed in U.S. Pat. Nos. 6,358,684; 5,863,727; 6,372,445; 6,221,606; 6,008,379; 5,945,526; 5,863,727; 5,800,996; 6,335,440; 6,008,373; 6,184,379; 6,140,494 and 5,656,554.

The carrier molecules and solid supports may comprise a linker that is used to covalently attach the substituents to the present ester. The solid support or carrier molecule may be directly attached (where Linker is a single bond) to the moieties or attached through a series of stable bonds. When the linker is a series of stable covalent bonds the linker typically incorporates 1-30 nonhydrogen atoms selected from the group consisting of C, N, O, S and P. When the linker is not a single covalent bond, the linker may be any combination of stable chemical bonds, optionally including, single, double, triple or aromatic carbon-carbon bonds, as well as carbon-nitrogen bonds, nitrogen-nitrogen bonds, carbon-oxygen bonds, sulfur-sulfur bonds, carbon-sulfur bonds, phosphorus-oxygen bonds, phosphorus-nitrogen bonds, and nitrogen-platinum bonds. Typically the linker incorporates less than 15 nonhydrogen atoms and are composed of any combination of ether, thioether, thiourea, amine, ester, carboxamide, sulfonamide, hydrazide bonds and aromatic or heteroaromatic bonds. Typically the linker is a combination of single carbon-carbon bonds and carboxamide, sulfonamide or thioether bonds. The bonds of the linker typically result in the following moieties that can be found in the linker: ether, thioether, carboxamide, thiourea, sulfonamide, urea, urethane, hydrazine, alkyl, aryl, heteroaryl, alkoxy, cycloalkyl and amine moieties. Examples of a linker include substituted or unsubstituted polymethylene, arylene, alkylarylene, arylenealkyl, or arylthio.

In one embodiment, the linker contains 1-6 carbon atoms; in another, the linker comprises a thioether linkage. Exemplary linking members include a moiety that includes —C(O)NH—, —C(O)O—, —NH—, —S—, —O—, and the like. In another embodiment, the linker is or incorporates the formula —(CH$_2$)$_d$(CONH(CH$_2$)$_e$)$_z$— or where d is an integer from 0-5, e is an integer from 1-5 and z is 0 or 1. In a further embodiment, the linker is or incorporates the formula —O—(CH$_2$)—. In yet another embodiment, the linker is or incorporates a phenylene or a 2-carboxy-substituted phenylene.

Detection of the present labeling reagent is performed using methods and reagents well known to those skilled in the art. A preferred method of detection of the invention is through the use of fluorescence. Fluorescence from the complex can be visualized with a variety of imaging techniques, including ordinary light or fluorescence microscopy, confocal laser-scanning microscopy, and flow cytometry, optionally using image deconvolution algorithms. Three-dimensional imaging resolution techniques in confocal microscopy utilize knowledge of the microscope's point spread function (image of a point source) to place out-of-focus light in its proper perspective. Multiple-reporter molecule target materials are optionally resolved spatially, chronologically, by size, or using detectably different spectral characteristics (including excitation and emission maxima, fluorescence intensity, fluorescence lifetime, fluorescence polarization, fluorescence photobleaching rates, or combinations thereof), or by combinations of these attributes. Typically, multiple-reporter molecule target materials are resolved using different labeling proteins with distinct spectral characteristics for each target material. Alternatively, the reporter molecules on the labeling proteins are the same but the samples are reporter molecule and viewed sequentially or are spatially separated.

Additionally, enzymes can be used where there occurs an enzyme-dependent secondary generation of signal, such as the formation of a colored product from a non-colored substrate. Enzyme reporter molecules or enzyme labeling systems are desirable in that they can achieve signal amplification and greater distinctions from backgrounds. The enzyme breaks down a substrate to produce a chromophore or fluorophore or other detectable signal, thus amplifying the sensitivity of the assay and, if the substrate yields a distinct product at or near its site of formation, visualizing the site of the antigen/antibody complex in the sample. The substrate is selected to yield the preferred measurable product. Chromogenic, fluorogenic and chemiluminescence-generating enzyme substrates are preferred. These enzymes are enzymes for which substrates yielding useful chromophores, fluorophores, or chemiluminescence are known. Such substrates are extensively used in the art and are described the MOLECULAR PROBES HANDBOOK OF FLUORES- CENT PROBES AND RESEARCH CHEMICALS by Richard P. Haugland, 10th Ed., (2005).

Preferred enzyme substrates of the invention are enzyme substrates that yield a fluorescent product that localizes at or near the site of enzyme activity. Enzymes of use in the method include any enzymes that utilize a chromogenic, fluorogenic, or chemiluminescence-generating substrate. Preferred enzymes of the invention include peroxidases, phosphatases, glycosidases, aequorins, or luciferases, and more specifically, HRP, *Coprinus cinereus* peroxidase, *Arthromyces ramosus* peroxidase, alkaline phosphatase, β-galactosidase, β-glucuronidase, or a protein A or protein G fusion protein of luciferase.

A preferred chromogenic (and in some cases fluorogenic) substrate and enzyme combination uses oxidoreductases such as horseradish peroxidase, *Coprinus cinereus* peroxidase, or *Arthromyces ramosus* peroxidase and a substrate such as 3,3'-diaminobenzidine (DAB) or 3-amino-9-ethylcarbazole (AEC), which yield a distinguishing color (brown and red, respectively). Other chromogenic oxidoreductase substrates that yield detectable products include, but are not limited to: 2,2'-azino-bis(3-ethylbenzthiazoline-6-sulfonic acid (ABTS), o-phenylenediamine (OPD), 3,3',5,5'-tetramethylbenzidine (TMB), o-dianisidine, 5-aminosalicylic acid, and 4-chloro-1-naphthol. Fluorogenic substrates include, but are not limited to, homovanillic acid or 4-hydroxy-3-methoxyphenylacetic acid, reduced phenoxazines and reduced benzothiazines, including the Amplex Red reagent and its variants (Miike, U.S. Pat. No. 4,384,042), reduced dihydroxanthenes, including the Amplex Gold reagent and other dihydrofluoresceins such as those described in U.S. Pat. No. 6,162,931, and dihydrorhodamines such as dihydrorhodamine 123. Peroxidase substrates that are tyramides, as described in U.S. Pat. Nos. 5,196,306; 5,583,001 and 5,731,158, which are incorporated by reference, represent a unique class of peroxidase substrates in that they can be intrinsically detectable before action of the enzyme but are "fixed in place" by the action of a peroxidase in the process termed tyramide signal amplification (TSA). These substrates, which are a preferred embodiment of the instant invention, are extensively utilized to reporter molecule targets in samples that are cells, tissues, or arrays for their subsequent detection by microscopy, flow cytometry, optical scanning, and fluorometry.

Another preferred chromogenic (and in some cases fluorogenic) substrate and enzyme combination uses a phosphatase enzyme such as calf intestinal alkaline phosphatase, an acid phosphatase, or a recombinant version of such a phosphatase in combination with a chromogenic substrate such as 5-bromo-4-chloro-3-indolyl phosphate (BCIP), 6-chloro-3-indolyl phosphate, 5-bromo-6-chloro-3-indolyl phosphate, p-nitrophenyl phosphate, or o-nitrophenyl phosphate or with a fluorogenic substrate such as 4-methylumbelliferyl phosphate, carboxyumbelliferyl phosphate, 6,8-difluoro-7-hydroxy-4-methylcoumarinyl phosphate (DiFMUP, U.S. Pat. No. 5,830,912), fluorescein diphosphate, 3-O-methylfluorescein phosphate, resorufin phosphate, 9H-(1,3-dichloro-9,9-dimethylacridin-2-one-7-yl) phosphate (DDAO phosphate), or ELF 97, ELF 39, or related phosphates (U.S. Pat. Nos. 5,316,906 and 5,443,986).

Glycosidases, in particularly β-galactosidase, β-glucuronidase, and β-glucosidase, are additional suitable enzymes. Appropriate chromogenic substrates include, but are not limited to, 5-bromo-4-chloro-3-indolyl β-D-galactopyranoside (X-gal) and similar indolyl galactosides, glucosides, and glucuronides, o-nitrophenyl β-D-galactopyranoside (ONPG), and p-nitrophenyl β-D-galactopyranoside. Preferred fluorogenic glycosidase substrates include resorufin β-D-galactopyranoside, fluorescein digalactoside (FDG), fluorescein diglucuronide and their structural variants (U.S. Pat. Nos. 5,208,148; 5,242,805; 5,362,628; 5,576,424 and 5,773,236), 4-methylumbelliferyl β-D-galactopyranoside, carboxyumbelliferyl β-D-galactopyranoside, and fluorinated coumarin β-D-galactopyranosides (U.S. Pat. No. 5,830,912).

Additional enzymes include, but are not limited to, hydrolases such as cholinesterases and peptidases, oxidases such as glucose oxidase and cytochrome oxidases, and reductases, for which suitable substrates are known.

When using florescent dyes to detect the desired target the sample is illuminated at a suitable absorption wavelength. A suitable wavelength is one that comes within the range of absorption wavelengths for each of the fluorescent dyes being used. Typically, the mixture is illuminated by a light source capable of producing light at or near the wavelength of maximum absorption of the dye or dyes, such as by ultraviolet or visible lamp, an arc lamp, a laser, or even sunlight. Illumination of the sample at a suitable wavelength results in one or more illuminated targets that are then analyzed according to the response of their fluorescence to the illumination. The illuminated targets are observed with any of a number of means for detecting a fluorescent response emitted from the illuminated target, including but not limited to visual inspection, cameras and film or other imaging equipment, or use of instrumentation such as fluorometers, plate readers, laser-based scanners, microscopes, or flow cytometers, or by means for amplifying the signal such as a photomultiplier (PMT).

In another embodiment, $R^a$ is:

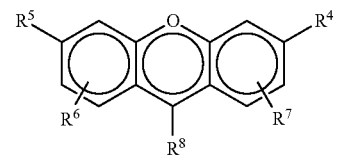

or a tautomer or salt thereof;

wherein, $R^4$, $R^5$, $R^6$, $R^7$, and $R^8$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3^-$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; or one or both of $R^4$ and $R^7$ and $R^5$ and $R^6$ are taken together to form a fused aryl or heteroaryl group; and one of $R^4$, $R^5$, $R^6$, $R^7$, and $R^8$ is the point of attachment to L through a covalent bond, -alkyl-, -substituted alkyl-, -alkenyl-, -substituted alkenyl-, -heterocyclyl-, -substituted heterocyclyl-, -aryl-, -substituted aryl-, -heteroaryl-, -substituted heteroaryl-, -cycloakyl-, -substituted cycloalkyl-, -oxy-, -alkoxy-, -substituted alkoxy-, -thio-, -amino-, or -substituted amino-.

More particularly, $R^4$ and $R^5$ are amino or imino. More particular still, $R^6$ and $R^7$ are H. In another embodiment $R^8$ is the point of attachment to L through a phenyl. More particularly, the phenyl is substituted with a carboxyl group. In a more particular embodiment thereof, $R^a$ is appended to L at the para or meta position, with respect to the xanthene moiety.

In a more particular embodiment thereof, $R^a$ has the following structure:

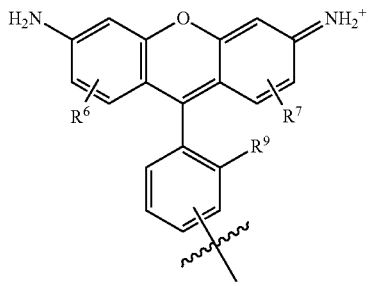

wherein the R groups are defined herein.
In another embodiment, $R^a$ is:

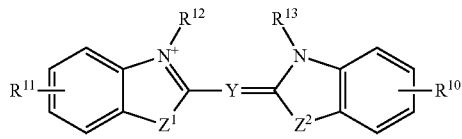

or a tautomer or salt thereof;
wherein,
$Z^1$ and $Z^2$ are each independently O, S, $NR^{17}$ or $CR^{18}R^{19}$;
Y is $-CR^{14}=(CR^{15}-CR^{16}=)_m$;
m is 0, 1, 2, or 3;
$R^{10}$ and $R^{11}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3^-$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl;
$R^{12}$, $R^{13}$ and $R^{17}$ are each independently H, alkyl, substituted alkyl, cycloalkyl, substituted cycloalkyl, aryl, substituted aryl, heteroaryl, substituted heteroaryl, heterocyclyl, substituted heterocyclyl; and
$R^{14}$, $R^{15}$ and $R^{16}$ are each independently, H, alkyl, substituted alkyl, cycloalkyl, substituted cycloalkyl, aryl, substituted aryl, heteroaryl, or substituted heteroaryl;
$R^{18}$ and $R^{19}$ are H, alkyl or substituted alkyl;
wherein one of $R^{10}$, $R^{11}$, $R^{12}$, $R^{13}$, $R^{14}$, $R^{15}$, $R^{16}$, $R^{17}$, $R^{18}$ and $R^{19}$ is the point of attachment to L through a covalent bond, -alkyl-, -substituted alkyl-, -alkenyl-, -substituted alkenyl-, -heterocyclyl-, -substituted heterocyclyl-, -aryl-, -substituted aryl-, -heteroaryl-, -substituted heteroaryl-, -cycloakyl-, -substituted cycloalkyl-, -oxy-, -alkoxy-, -substituted alkoxy-, -thio-, -amino-, or -substituted amino-.

In another more particular embodiment, $Z^1$ and $Z^2$ are both $CR^{18}R^{19}$. More particular still, $R^{18}$ and $R^{19}$ are both methyl. Alternatively, in a preferred embodiment $R^{19}$ is methyl and $R^{18}$ is the point of attachment to L through an -alkyl- or -substituted alkyl-. In another alternate embodiment, $R^{18}$ and $R^{19}$ are both methyl and the point of attachment to L is through an -alkyl- or -substituted alkyl- at $R^{13}$. More particular still, at least one or both of $R^{12}$ and $R^{13}$ are propanylsulfonate.

In another more particular embodiment, $R^a$ is:

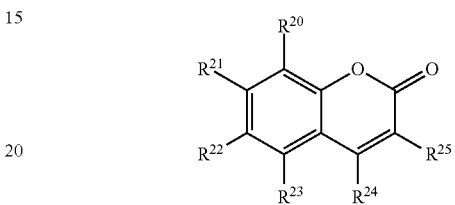

or a tautomer or salt thereof;
wherein,
$R^{20}$, $R^{21}$, $R^{22}$, $R^{23}$, $R^{24}$ and $R^{25}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3^-$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and
one of $R^{20}$, $R^{21}$, $R^{22}$, $R^{23}$, $R^{24}$ and $R^{25}$ is the point of attachment to L through a covalent bond, -alkyl-, -substituted alkyl-, -alkenyl-, -substituted alkenyl-, -heterocyclyl-, -substituted heterocyclyl-, -aryl-, -substituted aryl-, -heteroaryl-, -substituted heteroaryl-, -cycloakyl-, -substituted cycloalkyl-, -oxy-, -alkoxy-, -substituted alkoxy-, -thio-, -amino-, or -substituted amino-.

In another more particular embodiment, $R^a$ is:

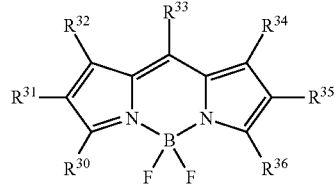

or a tautomer or salt thereof;
wherein,
$R^{30}$, $R^{31}$, $R^{32}$, $R^{33}$, $R^{34}$, $R^{35}$ and $R^{36}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3^-$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and one of $R^{30}$, $R^{31}$, $R^{32}$, $R^{33}$, $R^{34}$, $R^{35}$ and $R^{36}$ is the point of attachment to L through a covalent bond, -alkyl-, -substituted alkyl-, -alkenyl-, -substituted alkenyl-, -heterocyclyl-, -substituted heterocyclyl-, -aryl-, -substituted aryl-, -heteroaryl-, -substituted heteroaryl-, -cycloakyl-, -substituted cycloalkyl-, -oxy-, -alkoxy-, -substituted alkoxy-, -thio-, -amino-, or -substituted amino-.

In another more particular embodiment, $R^a$ is:

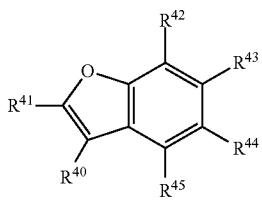

or a tautomer or salt thereof;
wherein,
$R^{40}$, $R^{41}$, $R^{42}$, $R^{43}$, $R^{44}$ and $R^{45}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3^-$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and one of $R^{40}$, $R^{41}$, $R^{42}$, $R^{43}$, $R^{44}$ and $R^{45}$ is the point of attachment to L through a covalent bond, -alkyl-, -substituted alkyl-, -alkenyl-, -substituted alkenyl-, -heterocyclyl-, -substituted heterocyclyl-, -aryl-, -substituted aryl-, -heteroaryl-, -substituted heteroaryl-, -cycloakyl-, -substituted cycloalkyl-, -oxy-, -alkoxy-, -substituted alkoxy-, -thio-, -amino-, or -substituted amino-.

Another aspect of the invention provides a compound of Formula II or a tautomer or salt thereof:

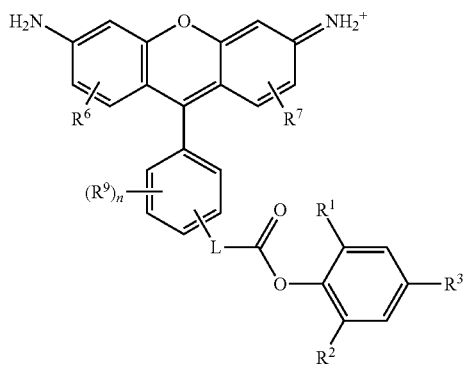

wherein,
L is a linker;
$R^1$ is a halogen;
$R^2$ is a halogen;
$R^3$ is a water solubilizing group;
$R^6$, $R^7$ and $R^9$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3^-$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and
n is 0, 1, or 2.

More particularly, $R^6$ and $R^7$ are H. In another embodiment $R^9$ is a carboxyl group.

In another more particular embodiment, L is a covalent bond, -alkyl-, -substituted alkyl-, -alkenyl-, -substituted alkenyl-, -heterocyclyl-, -substituted heterocyclyl-, -aryl-, -substituted aryl-, -heteroaryl-, -substituted heteroaryl-, -cycloakyl-, -substituted cycloalkyl-, -oxy-, -alkoxy-, -substituted alkoxy-, -thio-, -amino-, or -substituted amino-.

In another embodiment, $R^1$ and $R^2$ are chloro.
In another embodiment, $R^3$ is $—COO^-$, $—SO_3^-$, substituted azenyl, PEG, phosphate, or bisphosphonate. More particularly, $R^3$ is $—SO_3^-$.

In another embodiment, the compound of Formula II is a salt. More particularly, the salt comprises a potassium or sodium ion. In another embodiment, the compound of Formula II is soluble in an aqueous solution.

Another aspect of the invention provides a compound of Formula III or a tautomer or salt thereof:

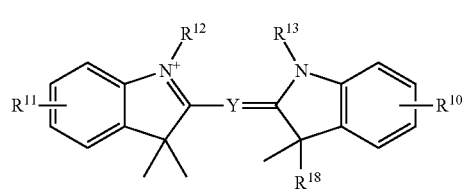

wherein,
Y is $—CR^{14}=(CR^{15}—CR^{16}=)_m$;
m is 0, 1, 2, or 3;
$R^{10}$ and $R^{11}$ are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3^-$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl;
$R^{12}$ and $R^{13}$ are each independently H, alkyl, substituted alkyl, cycloalkyl, substituted cycloalkyl, aryl, substituted aryl, heteroaryl, substituted heteroaryl, heterocyclyl, substituted heterocyclyl;

$R^{18}$ is methyl; and wherein one of $R^{13}$ or $R^{18}$ is:

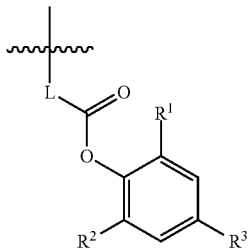

L is a linker;

$R^1$ is a halogen;

$R^2$ is a halogen; and $R^3$ is a water solubilizing group.

More particularly, $R^1$ and $R^2$ are chloro. More particular still, $R^3$ is $-SO_3^-$. More particular still, $R^{18}$ and $R^{19}$ are both methyl. In a preferred embodiment $R^{19}$ is methyl and $R^{18}$ is the point of attachment to L through an -alkyl- or -substituted alkyl-. In another alternate embodiment, $R^{18}$ and $R^{19}$ are both methyl and the point of attachment to L is through an -alkyl- or -substituted alkyl- at $R^{13}$.

In another more particular embodiment, L is a covalent bond, -alkyl-, -substituted alkyl-, -alkenyl-, -substituted alkenyl-, -heterocyclyl-, -substituted heterocyclyl-, -aryl-, -substituted aryl-, -heteroaryl-, -substituted heteroaryl-, -cycloakyl-, -substituted cycloalkyl-, -oxy-, -alkoxy-, -substituted alkoxy-, -thio-, -amino-, or -substituted amino-.

In another more particular embodiment, $R^a$ is:

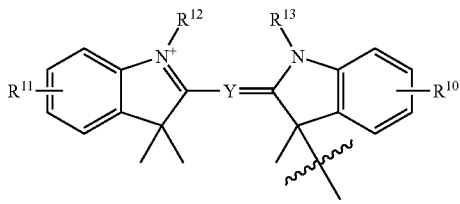

wherein the R-groups are defined herein.

Another aspect of the invention provides a compound selected from the group consisting of:

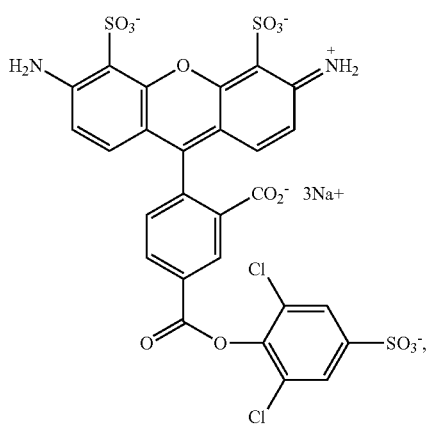

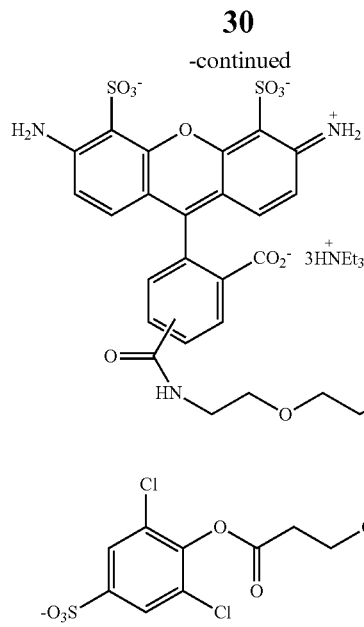

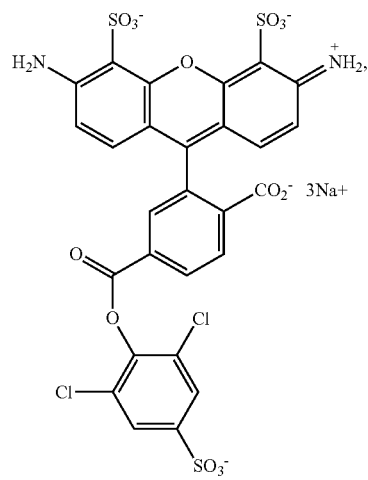

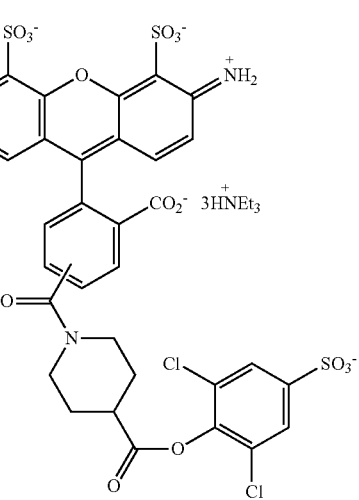

, and

-continued

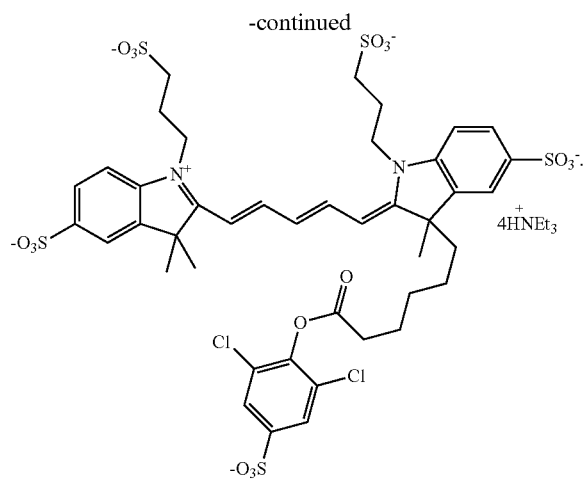

Another aspect of the invention provides a compound having the following structure or a tautomer or salt thereof:

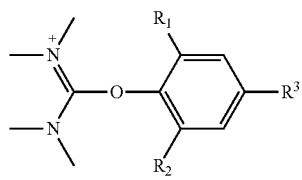

wherein,
$R^1$ is a halogen;
$R^2$ is a halogen; and
$R^3$ is a water solubilizing group.

In another embodiment, $R^1$ and $R^2$ are chloro. More particularly, $R^3$ is $—SO_3^-$.

In a preferred embodiment, any one of the aforementioned compounds is used in the methods described below.

Preparation of Conjugates

In another embodiment is provided a method for forming conjugates of the present reporter molecules and a carrier molecule or solid support. This method comprises:
a) combining a reporter molecule with a carrier molecule or solid support to form a combined sample, wherein the compound comprises a reactive group as described herein, such as the compound of Formula IA; and,
b) incubating the combined sample for a sufficient amount of time for the compound to form a covalent bond with either the carrier molecule or solid support whereby a conjugate is formed.

The conjugates of the carrier molecules or solid supports, e.g., drugs, peptides, toxins, nucleotides, phospholipids and other organic molecules are prepared by organic synthesis methods using the reactive dyes of the invention and are generally prepared by means well recognized in the art (Haugland, MOLECULAR PROBES, supra, (2005)). Preferably, conjugation to form a covalent bond consists of simply mixing the reactive compounds of the present invention in a suitable solvent in which both the reactive compound and the substance to be conjugated are soluble. The reaction preferably proceeds spontaneously without additional reagents at room temperature or below. Chemical modification of water-insoluble substances, so that a desired compound-conjugate may be prepared, is preferably performed in an aprotic solvent such as dimethylformamide, dimethylsulfoxide, acetone, ethyl acetate, toluene, or chloroform. Similar modification of water-soluble materials is readily accomplished through the use of the compounds of the present invention to make them more readily soluble in organic solvents.

Preparation of peptide or protein conjugates typically comprises first dissolving the protein to be conjugated in aqueous buffer at about.1-10 mg/mL at room temperature or below. Bicarbonate buffers (pH about 8.3) are especially suitable for reaction with succinimidyl esters, phosphate buffers (pH about 7.2-8) for reaction with thiol-reactive functional groups and carbonate or borate buffers (pH about 9) for reaction with isothiocyanates and dichlorotriazines. The appropriate reactive compound is then dissolved in a nonhydroxylic solvent (usually DMSO or DMF) in an amount sufficient to give a suitable degree of conjugation when added to a solution of the protein to be conjugated. The appropriate amount of compound for any protein or other component is conveniently predetermined by experimentation in which variable amounts of the compound are added to the protein, the conjugate is chromatographically purified to separate unconjugated compound and the compound-protein conjugate is tested in its desired application.

Following addition of the reactive compound to the component solution, the mixture is incubated for a suitable period (typically about 1 hour at room temperature to several hours on ice), the excess compound is removed by gel filtration, dialysis, HPLC, adsorption on an ion exchange or hydrophobic polymer or other suitable means. The compound-conjugate is used in solution or lyophilized. In this way, suitable conjugates can be prepared from antibodies, antibody fragments, avidins, lectins, enzymes, proteins A and G, cellular proteins, albumins, histones, growth factors, hormones, and other proteins.

Conjugates of polymers, including biopolymers and other higher molecular weight polymers are typically prepared by means well recognized in the art (for example, Brinkley et al., Bioconjugate Chem., 3: 2 (1992)). In these embodiments, a single type of reactive site may be available, as is typical for polysaccharides) or multiple types of reactive sites (e.g. amines, thiols, alcohols, phenols) may be available, as is typical for proteins. Selectivity of labeling is best obtained by selection of an appropriate reactive dye. For example, modification of thiols with a thiol-selective reagent such as a haloacetamide or maleimide, or modification of amines with an amine-reactive reagent such as an activated ester, acyl azide, isothiocyanate or 3,5-dichloro-2,4,6-triazine. Partial selectivity can also be obtained by careful control of the reaction conditions.

When modifying polymers with the compounds, an excess of compound is typically used, relative to the expected degree of compound substitution. Any residual, unreacted compound or a compound hydrolysis product is typically removed by dialysis, chromatography or precipitation. Presence of residual, unconjugated dye can be detected by thin layer chromatography using a solvent that elutes the dye away from its conjugate. In all cases it is usually preferred that the reagents be kept as concentrated as practical so as to obtain adequate rates of conjugation.

In an exemplary embodiment, the conjugate of the invention is associated with an additional substance, that binds either to the fluorophore or the conjugated substance (carrier molecule or solid support) through noncovalent interaction. In another exemplary embodiment, the additional substance is an antibody, an enzyme, a hapten, a lectin, a receptor, an oligonucleotide, a nucleic acid, a liposome, or a polymer. The additional substance is optionally used to probe for the location of the conjugate, for example, as a means of enhancing the signal of the conjugate.

Another aspect of the invention provides a method of making a compound of Formula I comprising:

contacting a carrier molecule or a solid support comprising a nucleophile with a compound of Formula IA or a tautomer or salt thereof:

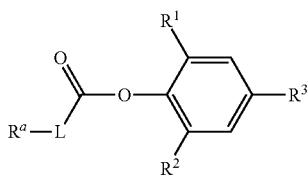

wherein,
L is a linker;
R$^1$ is a halogen;
R$^2$ is a halogen;
R$^3$ comprises a water solubilizing group; and
R$^a$ is a reporter molecule;
forming a compound of Formula I or a tautomer or salt thereof:

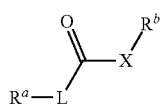

wherein,
L is the linker;
R$^a$ is the reporter molecule; and
R$^b$ is the carrier molecule or solid support comprising a nucleophile (X).

In another more particular embodiment, L is a covalent bond, -alkyl-, -substituted alkyl-, -alkenyl-, -substituted alkenyl-, -heterocyclyl-, -substituted heterocyclyl-, -aryl-, -substituted aryl-, -heteroaryl-, -substituted heteroaryl-, -cycloakyl-, -substituted cycloalkyl-, -oxy-, -alkoxy-, -substituted alkoxy-, -thio-, -amino-, or -substituted amino-.

In another embodiment, R$^1$ and R$^2$ are chloro.

In another embodiment, R$^3$ is —COO$^-$, —SO$_3^-$, substituted azenyl, PEG, phosphate, or bisphosphonate. More particularly, R$^3$ is —SO$_3^-$.

In another embodiment, R$^a$ is a dye. More particularly, the dye is a xanthene, a cyanine, an indole, a benzofuran, a coumarin, or a borapolyazaindacine.

In another embodiment, R$^a$ is a chelating moiety, a hapten, an antibody, an enzyme, a radiolabeled, a metal ion or metal ion containing substance, a pigment, a chromogen, a phosphor, a fluorogen, a bioluminescent substance, a chemiluminescent substance, or a semiconductor nanocrystal. More particularly, R$^a$ is avidin, streptavidin or an analog thereof.

In another embodiment, the compound of Formula IA is a salt. More particularly, the salt comprises a potassium or sodium ion.

In another embodiment, the reporter molecule is hydrophobic. In another embodiment, the compound of Formula IA is soluble in an aqueous solution. Accordingly, the SDP ester solubilizes hydrophobic reporter molecules in aqueous solution, thereby permitting reaction with hydrophilic carrier molecules and supports in aqueous solutions, where organic solvents may lead to disruption or denaturing of the native structure of the molecules.

In another embodiment, R$^b$ is a solid support. More particularly, R$^b$ is a column or gel. Alternatively, R$^b$ is a carrier molecule. More particular still, the carrier molecule is selected from the group consisting of an amino acid, a peptide, a protein, a carbohydrate, a polysaccharide, a nucleoside, a nucleotide, an oligonucleotide, a nucleic acid polymer, a drug, a lipid, and a synthetic polymer. More particularly, the carrier molecule is a protein.

Another embodiment of the invention, further comprises incubating the carrier molecule or solid support with the compound of Formula IA after the contacting step.

In another embodiment, the contacting step is done in an aqueous solution.

In another embodiment, X is an amino, thio, or oxo group.

Another aspect of the invention provides a method of labeling a carrier molecule or solid support comprising:
contacting the carrier molecule or solid support with a compound of Formula IA or a tautomer or salt thereof:

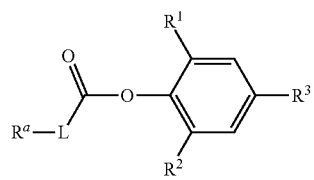

wherein,
L is a linker;
R$^1$ is a halogen;
R$^2$ is a halogen;
R$^3$ comprises a water solubilizing group;
R$^a$ is a reporter molecule; and
the carrier molecule or solid support comprises a nucleophile; and
forming a reporter molecule carrier molecule or solid support.

In a more particular embodiment, the labeled carrier molecule or solid support comprises a compound of Formula I:

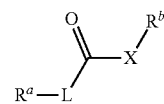

wherein,
R$^a$ is the reporter molecule; and
R$^b$ is the carrier molecule or solid support comprising a nucleophile (x).

Another aspect of the invention provides a method of making a compound of Formula IA or a tautomer or salt thereof comprising:
contacting a compound of Formula IB or a tautomer or salt thereof:

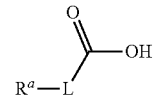

with a compound of Formula IC or a tautomer or salt thereof:

IC and forming the compound of Formula IA or a tautomer or salt thereof:

IA wherein,
R$^1$ is a halogen;
R$^2$ is a halogen;
R$^3$ comprises a water solubilizing group;
L is a linker; and
R$^a$ is a reporter molecule.

In a more particular embodiment, the contacting step is done in the presence of dimethylaminopyridine (DMAP). In another embodiment, the contacting step is done in an organic solvent.

In general, compounds of the invention are generally prepared by condensation of a phenol of the formula:

XI

With a reporter molecule contain a carboxylic acid in organic or aqueous/organic solvent systems. The carboxylic acid can be activated in situ with a reagent such as a carbodiimide, followed by reaction with the phenol XI. The carboxylic acid can also be activated by conversion to an electrophilic equivalent such as an acid chloride, followed by reaction with the phenol XI.

A1

Alternatively, the phenol XI can be activated by conversion into a uranium salt, either preparatively or in situ, followed by reaction with a carboxylic acid; this reaction can be facilitated by a catalyst such as 4-dimethylaminopyridine (DMAP).

A1

Carrier Molecules

A variety of carrier molecules are useful in the present invention. Exemplary carrier molecules include antigens, steroids, vitamins, drugs, haptens, metabolites, toxins, environmental pollutants, amino acids, peptides, proteins, nucleic acids, nucleic acid polymers, carbohydrates, lipids, and polymers.

In an exemplary embodiment, the carrier molecule comprises an amino acid, a peptide, a protein, a polysaccharide, a nucleoside, a nucleotide, an oligonucleotide, a nucleic acid, a hapten, a psoralen, a drug, a hormone, a lipid, a lipid assembly, a synthetic polymer, a polymeric microparticle, a biological cell, a virus and combinations thereof. In another exemplary embodiment, the carrier molecule is selected from a hapten, a nucleotide, an oligonucleotide, a nucleic acid polymer, a protein, a peptide or a polysaccharide. In another exemplary embodiment, at least one R-group member (such as one of R$^1$-R$^{45}$) comprise a carrier molecule. In another exemplary embodiment one of the R-group members comprises a solid support.

In an exemplary embodiment, the carrier molecule comprises an amino acid, a peptide, a protein, a polysaccharide, a nucleoside, a nucleotide, an oligonucleotide, a nucleic acid, a hapten, a psoralen, a drug, a hormone, a lipid, a lipid assembly, a synthetic polymer, a polymeric microparticle, a biological cell, a virus and combinations thereof. In another exemplary embodiment, the carrier molecule is selected from a hapten, a nucleotide, an oligonucleotide, a nucleic acid polymer, a protein, a peptide or a polysaccharide. In a preferred embodiment the carrier molecule is amino acid, a peptide, a protein, a polysaccharide, a nucleoside, a nucleotide, an oligonucleotide, a nucleic acid, a hapten, a psoralen, a drug, a hormone, a lipid, a lipid assembly, a tyramine, a synthetic polymer, a polymeric microparticle, a biological cell, cellular components, an ion chelating moiety, an enzymatic substrate or a virus. In another preferred embodiment, the carrier molecule is an antibody or fragment thereof, an antigen, an avidin or streptavidin, a biotin, a dextran, an antibody binding protein, a fluorescent protein, agarose, and a non-biological microparticle. Typically, the carrier molecule is an antibody, an antibody fragment, antibody-binding proteins, avidin, streptavidin, a toxin, a lectin, or a growth factor. Preferred haptens include biotin, digoxigenin and fluorophores.

Antibody binging proteins include, but are not limited to, protein A, protein G, soluble Fc receptor, protein L, lectins, anti-IgG, anti-IgA, anti-IgM, anti-IgD, anti-IgE or a fragment thereof.

In an exemplary embodiment, the enzymatic substrate is selected from an amino acid, peptide, sugar, alcohol, alkanoic acid, 4-guanidinobenzoic acid, nucleic acid, lipid, sulfate, phosphate, —$CH_2OCOalkyl$ and combinations thereof. Thus, the enzyme substrates can be cleave by enzymes selected from the group consisting of peptidase, phosphatase, glycosidase, dealkylase, esterase, guanidinobenzotase, sulfatase, lipase, peroxidase, histone deacetylase, endoglycoceramidase, exonuclease, reductase and endonuclease.

In another exemplary embodiment, the carrier molecule is an amino acid (including those that are protected or are substituted by phosphates, carbohydrates, or $C_1$ to $C_{22}$ carboxylic acids), or a polymer of amino acids such as a peptide or protein. In a related embodiment, the carrier molecule contains at least five amino acids, more preferably 5 to 36 amino acids. Exemplary peptides include, but are not limited to, neuropeptides, cytokines, toxins, protease substrates, and protein kinase substrates. Other exemplary peptides may function as organelle localization peptides, that is, peptides that serve to target the conjugated compound for localization within a particular cellular substructure by cellular transport mechanisms. Preferred protein carrier molecules include enzymes, antibodies, lectins, glycoproteins, histones, albumins, lipoproteins, avidin, streptavidin, protein A, protein G, phycobiliproteins and other fluorescent proteins, hormones, toxins and growth factors. Typically, the protein carrier molecule is an antibody, an antibody fragment, avidin, streptavidin, a toxin, a lectin, or a growth factor. Exemplary haptens include biotin, digoxigenin and fluorophores.

In another exemplary embodiment, the carrier molecule comprises a nucleic acid base, nucleoside, nucleotide or a nucleic acid polymer, optionally containing an additional linker or spacer for attachment of a fluorophore or other ligand, such as an alkynyl linkage (U.S. Pat. No. 5,047,519), an aminoallyl linkage (U.S. Pat. No. 4,711,955) or other linkage. In another exemplary embodiment, the nucleotide carrier molecule is a nucleoside or a deoxynucleoside or a dideoxynucleoside.

Exemplary nucleic acid polymer carrier molecules are single- or multi-stranded, natural or synthetic DNA or RNA oligonucleotides, or DNA/RNA hybrids, or incorporating an unusual linker such as morpholine derivatized phosphates (AntiVirals, Inc., Corvallis Oreg.), or peptide nucleic acids such as N-(2-aminoethyl)glycine units, where the nucleic acid contains fewer than 50 nucleotides, more typically fewer than 25 nucleotides.

In another exemplary embodiment, the carrier molecule comprises a carbohydrate or polyol that is typically a polysaccharide, such as dextran, FICOLL, heparin, glycogen, amylopectin, mannan, inulin, starch, agarose and cellulose, or is a polymer such as a poly(ethylene glycol). In a related embodiment, the polysaccharide carrier molecule includes dextran, agarose or FICOLL.

In another exemplary embodiment, the carrier molecule comprises a lipid (typically having 6-25 carbons), including glycolipids, phospholipids, and sphingolipids. Alternatively, the carrier molecule comprises a lipid vesicle, such as a liposome, or is a lipoprotein (see below). Some lipophilic substituents are useful for facilitating transport of the conjugated dye into cells or cellular organelles.

Alternatively, the carrier molecule is cells, cellular systems, cellular fragments, or subcellular particles. Examples of this type of conjugated material include virus particles, bacterial particles, virus components, biological cells (such as animal cells, plant cells, bacteria, or yeast), or cellular components. Examples of cellular components that can be labeled, or whose constituent molecules can be labeled, include but are not limited to lysosomes, endosomes, cytoplasm, nuclei, histones, mitochondria, Golgi apparatus, endoplasmic reticulum and vacuoles.

In another embodiment the carrier molecule is a metal chelating moiety. While any chelator that binds a metal ion of interest and gives a change in its fluorescence properties is a suitable conjugate, preferred metal chelating moieties are crown ethers, including diaryldiaza crown ethers, as described in U.S. Pat. No. 5,405,975 to Kuhn et al. (1995); derivatives of 1,2-bis-(2-aminophenoxyethane)-N,N,N',N'-tetraacetic acid (BAPTA), as described in U.S. Pat. No. 5,453,517 to Kuhn et al. (1995) (incorporated by reference) and U.S. Pat. No. 5,049,673 to Tsien et al. (1991); derivatives of 2-carboxymethoxy-aniline-N,N-diacetic acid (APTRA), as described by Ragu et al., *Am. J. Physiol.,* 256: C540 (1989); and pyridyl-based and phenanthroline metal ion chelators, as described in U.S. Pat. No. 5,648,270 to Kuhn et al. (1997).

Esters of the present invention are optionally prepared in chemically reactive forms and further conjugated to polymers such as dextrans to improve their utility as sensors as described in U.S. Pat. Nos. 5,405,975 and 5,453,517.

In another exemplary embodiment, the carrier molecule non-covalently associates with organic or inorganic materials. Exemplary embodiments of the carrier molecule that possess a lipophilic substituent can be used to target lipid assemblies such as biological membranes or liposomes by non-covalent incorporation of the dye compound within the membrane, e.g., for use as probes for membrane structure or for incorporation in liposomes, lipoproteins, films, plastics, lipophilic microspheres or similar materials.

In an exemplary embodiment, the carrier molecule comprises a specific binding pair member wherein the present compounds are conjugated to a specific binding pair member and are used to detect an analyte in a sample. Alternatively, the presence of the labeled specific binding pair member indicates the location of the complementary member of that specific binding pair; each specific binding pair member having an area on the surface or in a cavity which specifically binds to, and is complementary with, a particular spatial and polar organization of the other. Exemplary binding pairs are set forth in Table 2.

TABLE 2

Representative Specific Binding Pairs

| antigen | antibody |
| --- | --- |
| biotin | avidin (or streptavidin or anti-biotin) |
| IgG* | protein A or protein G |
| drug | drug receptor |
| folate | folate binding protein |
| toxin | toxin receptor |
| carbohydrate | lectin or carbohydrate receptor |
| peptide | peptide receptor |
| protein | protein receptor |
| enzyme substrate | enzyme |
| DNA (RNA) | cDNA (cRNA)† |
| hormone | hormone receptor |
| ion | chelator |
| antibody | antibody-binding proteins |

*IgG is an immunoglobulin
†cDNA and cRNA are the complementary strands used for hybridization Solid Supports In an exemplary embodiment, the compounds of the invention are bonded to a solid support, which includes semi-solid supports. A solid support suitable for use in the present invention is typically substantially insoluble in liquid phases. Solid supports of the current invention are not limited to a specific type of support. Rather, a large number of supports are available and are known to one of ordinary skill in the art. Thus, useful solid supports include semi-solids, such as aerogels and hydrogels, resins, beads, biochips (including thin film coated biochips), multi-well plates (also referred to as microtitre plates), membranes, conducting and nonconducting metals and magnetic supports. More specific examples of useful solid supports include silica gels, polymeric membranes, particles, derivatized plastic films, glass beads, cotton, plastic beads, alumina gels, polysaccharides such as Sepharose, poly(acrylate), polystyrene, poly(acrylamide), polyol, agarose, agar, cellulose, dextran, starch, FICOLL, heparin, glycogen, amylopectin, mannan, inulin, nitrocellulose, diazocellulose, polyvinylchloride, polypropylene, polyethylene (including poly(ethylene glycol)), nylon, latex bead, magnetic bead, paramagnetic bead, superparamagnetic bead, starch and the like.

In some embodiments, the solid support may include a solid support reactive functional group, including, but not limited to, hydroxyl, carboxyl, amino, thiol, aldehyde, halogen, nitro, cyano, amido, urea, carbonate, carbamate, isocyanate, sulfone, sulfonate, sulfonamide, sulfoxide, etc., for attaching the compounds of the invention. In a preferred embodiment, the solid supports contain a nucleophile (x), such as amino, thiol, or hydroxyl.

A suitable solid phase support can be selected on the basis of desired end use and suitability for various synthetic protocols. For example, where amide bond formation is desirable to attach the compounds of the invention to the solid support, resins generally useful in peptide synthesis may be employed, such as polystyrene (e.g., PAM-resin obtained from Bachem Inc., Peninsula Laboratories, etc.), POLYHIPE™ resin (obtained from Aminotech, Canada), polyamide resin (obtained from Peninsula Laboratories), polystyrene resin grafted with polyethylene glycol (Tenta-Gel™, Rapp Polymere, Tubingen, Germany), polydimethylacrylamide resin (available from Milligen/Biosearch, California), or PEGA beads (obtained from Polymer Laboratories).

Methods of Using the Present Labeling Reagents:

In one embodiment, the present invention provides methods of using the compounds described herein to detect or monitor an analyte in a sample or assay. In other embodiments, the compounds of the present invention are utilized to label a sample or analyte to give a detectable or traceable optical response under desired conditions by a) preparing a labeling solution comprising a compound of Formula I as described above, at a concentration sufficient to yield a detectable optical response under the desired conditions; combining the sample solution for a period of time sufficient for the dye compound to yield a detectable response under the desired conditions; and c) detecting the optical response, preferably by illumination. Optionally, the sample is washed to remove residual, excess or unbound label. The compound typically forms a covalent or non-covalent association or complex with an element of the sample, or is simply present within the bounds of the sample or portion of the sample.

In one embodiment, the compound of Formula I is used to determine a specified characteristic of the sample by further comparing the optical response with a standard or expected response. For example, the dye solution is used to monitor specific components of the sample with respect to their spatial and temporal distribution in the sample.

In a particular embodiment, wherein a solid support is labeled with labeling reagent of present invention (such as a compound of Formula IA), the reporter molecule is a ligand or receptor and the support forms a column, thereby forming an affinity column. In a preferred embodiment the support is in a bead form. More particularly, the bead is a magnetic bead.

For biological applications, the solution is typically an aqueous or mostly aqueous solution that comprises one or more of the described compounds. In one aspect of the invention, the solution comprises a fluorophore as described above; alternatively, the dye solution comprises a hapten.

In an exemplary application of the present method, different features of an analyte, e.g., a cell or epitopes of a molecule, are labeled with different colored fluorescent conjugates. The target is detected and its identity is confirmed using the colocalization or "coincidence" of each color on each target. Coincidence staining allows for the detection and differentiation of different organisms or strains of organisms expressing different surface markers. Moreover, coincidence staining provides a method of distinguishing molecules of different structure down to the level of isomeric differences and differences in stereochemistry.

In the detection of pathogenesis, the most direct analyte is the pathogenic organism itself. In this case, assays preferably identify particular features of the organism such as surface proteins. To further aid in characterization, it is preferred to assay for molecular analytes as well. An example of a molecular analyte is an exotoxin such as cholera toxin. Antigen specific binding receptors are generated that recognize different characteristics of an analyte with high specificity. In the case of molecular analytes, receptors recognize different epitopes of a protein or small molecule, while cellular analytes are recognized through different molecules on the cell surface.

Although the fluorescence from each conjugate can be detected simultaneously, in one embodiment, to facilitate coincidence staining, the fluorescence from each analyte is detected independently.

In another exemplary embodiment, colocalization is used to differentiate between the formation of an analyte-conjugate complex and non-specific binding of the analyte to another species within the assay system. The intrinsic sensitivity of an assay often is limited by non-specific binding of the analyte or other assay mixture components to the substrate. Single analyte coincidence staining can be used to differentiate between specific binding of the analyte to the conjugate and non-specific binding of assay mixture components to the conjugate based on the colocalization of fluorescent conjugate colors. Those of skill in the art will appreciate that coincidence staining as described herein is useful to distinguish non-specific binding in both solid-phase (e.g., gene chip) and solution-based assays Coincidence staining can also be used to identify a single analyte. For example, one may wish to confirm the presence of a selected analyte in a mixture of analytes that are structurally similar (e.g. having a common epitope) or that have similar affinity for the component of the conjugate. In such circumstances, it may prove that the detection of a single epitope is not sufficient for conclusive identification of a target. Measuring the level of 2, preferably 3, more preferably 4 and even more preferably 5 or more markers within a single analyte, provides an unambiguous profile specific for the analyte of interest.

In another exemplary embodiment, the present invention provides a method for distinguishing between organisms expressing the same surface markers. Using coincidence staining, it is possible to identify differences in targets based on the ratio of surface marker expression. For example, despite intense efforts, no single binding-receptor has been found for the unambiguous detection of *B. anthracis* spores, due to extensive cross-reactivity with related *B. cereus* and *B. thuringiensis*, which are gen Kits Additional embodiments of the present invention include kits comprising the labeling reagents described herein for use in labeling carrier molecules or solid supports. In addition to the compounds, the kits include instructions on how to reporter molecule the carrier molecule or solid support. One particular embodiment provides a kit for forming a conjugate with a carrier molecule or solid support and a labeling reagent, wherein the kit comprises:

a) a labeling reagent according to Formula IA or a tautomer or salt thereof:

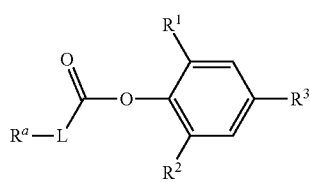

IA wherein,
L is a linker;
$R^1$ is a halogen;
$R^2$ is a halogen;
$R^3$ comprises a water solubilizing group; and
$R^a$ is a reporter molecule;
b) instructions for forming a conjugate with the carrier molecule or solids support.

Various ancillary materials will frequently be employed in an assay in accordance with the present invention. In an exemplary embodiment, buffers and/or stabilizers are present in the kit components. In another exemplary embodiment, the kits comprise indicator solutions or indicator "dipsticks", blotters, culture media, cuvettes, and the like. In yet another exemplary embodiment, the kits comprise indicator cartridges (where a kit component is bound to a solid support) for use in an automated detector. In another exemplary embodiment, the kit further comprises molecular weight markers, wherein said markers are selected from phosphorylated and non-phosphorylated polypeptides, calcium-binding and non-calcium binding polypeptides, sulfonated and non-sulfonated polypeptides, and sialylated and non-sialylated polypeptides. In another exemplary embodiment, the kit further comprises a member selected from a fixing solution, a detection reagent, a standard, a wash solution, and combinations thereof.

A detailed description of the invention having been provided above, the following examples are given for the purpose of illustrating the invention and shall not be construed as being a limitation on the scope of the invention or claims.

EXAMPLES

Example 1. BODIPY Ester of 2,6-Difluoroactivated Phenol, Solubilized with Sulfo Group (Compound 4)

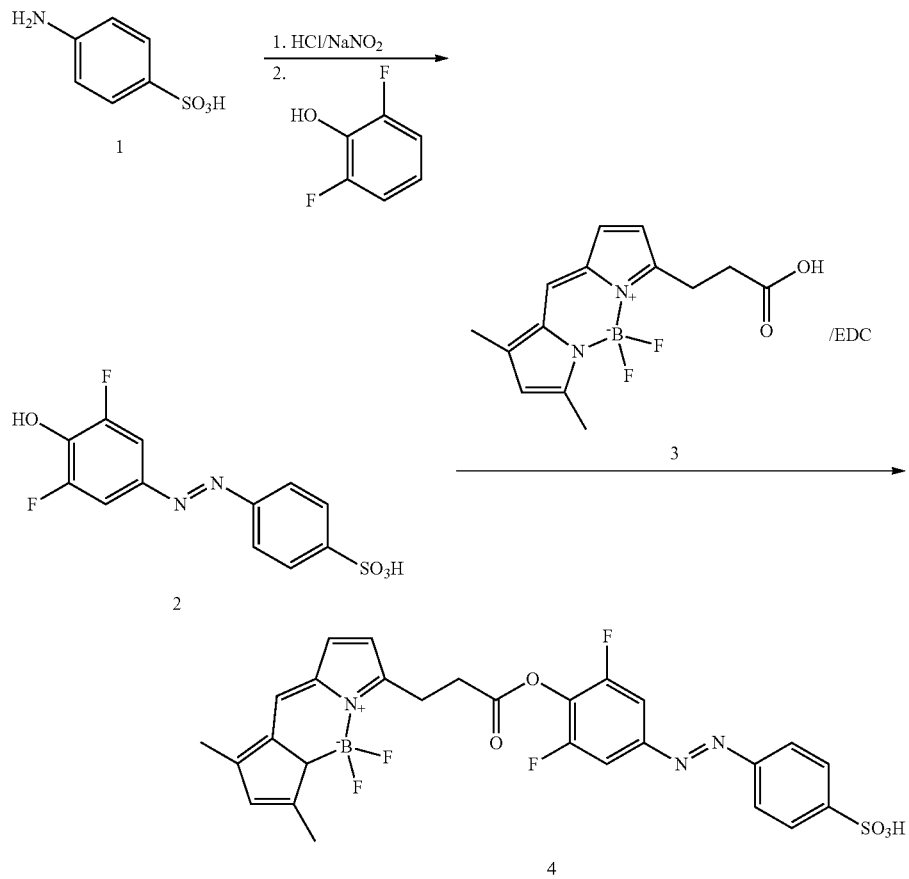

4-((3,5-difluoro-4-hydroxyphenyl)diazenyl)benzenesulfonic acid (2)

Sulfanilic acid (0.767 g, 4.43 mmol) was dissolved in hot mixture of 20 mL of water and 10 mL of conc. HCl. The solution was cooled in ice/NaCl bath to 0° C. giving a suspension of HCl salt. The solution of sodium nitrite (0.367 g, 5.32 mmol in 5 mL of water) was added dropwise to the suspension of ammonium salt, maintaining the temperature below +5° C. All solid dissolved and the resulting solution was stirred for 20 min. After that white precipitate formed again and the resulting suspension was added dropwise to the mixture of 2,6-difluorophenol (0.576 g, 4.43 mmol) in 10 mL of dioxane and KOH (10 g) in 15 mL of water, cooled in ice/water bath. The reaction mixture was stirred for 30 min in ice/water bath and then extracted with ethyl acetate (3×30 mL). The aqueous solution was acidified with 10% HCl to pH 2-3 and the formed yellow precipitate was collected, washed with water and dried in vacuum to give phenol 2 as a yellow powder (1.1 g, 79%).

3-(3-(2,6-Difluoro-4-((4-sulfophenyl)diazenyl)phenoxy)-3-oxopropyl)-5,5-difluoro-7,9-dimethyl-5H-dipyrrolo[1,2-c:1',2'-f][1,3,2]diazaborinin-4-ium-5-uide (4)

Acid 3 (0.019 g, 0.065 mmol) and phenol 2 (0.020 g, 0.064 mmol) were dissolved in 2 mL of dry DMF. EDC (0.015 g, 0.078 mmol) was added to the solution and the reaction mixture was stirred overnight at rt. Then it was concentrated in vacuum and the crude product was purified by column chromatography on silica gel using 60:10:1 chloroform-methanol-acetic acid as an eluant to give ester 4 as an orange powder (0.015 g, 39%).

Example 2: BODIPY Ester of 2,6-Dichloro Activated Phenol, Solubilized with Two Carboxylic Groups (Compound 8)

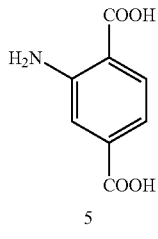
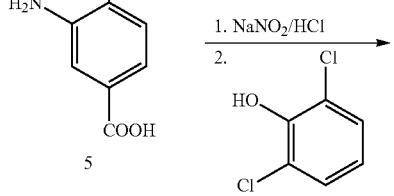

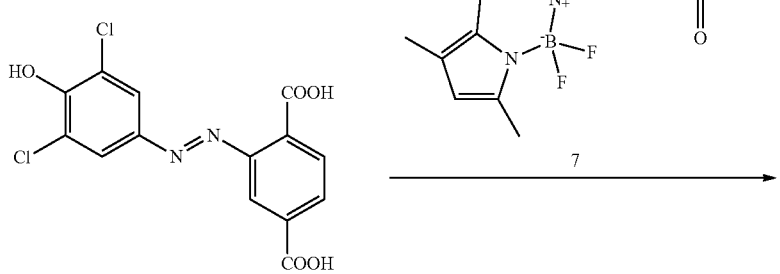

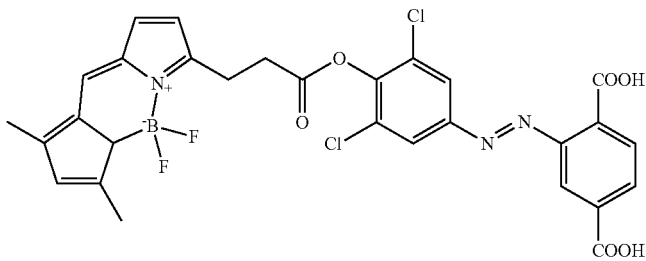

2-((3,5-Dichloro-4-hydroxyphenyl)diazenyl)terephthalic acid (6)

2-Aminoterephtalic acid (0.500 g, 2.76 mmol) was dissolved in hot mixture of 30 mL of water and 10 mL of conc. HCl. The solution was cooled in ice/NaCl bath to 0° C. giving a suspension of HCl salt. The solution of sodium nitrite (0.230 g, 3.33 mmol in 10 mL of water) was added dropwise to the suspension of ammonium salt, maintaining the temperature below +5° C. The resulting solution was stirred for 20 min and added dropwise to the solution of 2,6-dichlorophenol (0.450 g, 2.76 mmol) in 80 mL of 2M KOH, cooled in ice/water bath. The reaction mixture was stirred for 2 hrs in ice/water bath and then acidified with 10% HCl to pH 2-3 and extracted with ethyl acetate (3×30 mL). The combined extract was washed with brine (30 mL), dried over $Na_2SO_4$ and evaporated. The crude product was purified by column chromatography on silica gel using 60:15:1 chloroform-methanol-acetic acid as an eluant to give phenol 6 as a orange solid (0.200 g, 20%).

3-(3-(2,6-Dichloro-4-((2,5-dicarboxyphenyl)diazenyl)phenoxy)-3-oxopropyl)-5,5-difluoro-7,9-dimethyl-5H-dipyrrolo[1,2-c:1',2'-f][1,3,2]diazaborinin-4-ium-5-uide (8)

3-(2-Carboxyethyl)-5,5-difluoro-7,9-dimethyl-5H-dipyrrolo[1,2-c:1',2'-f][1,3,2]diazaborinin-4-ium-5-uide (3, 0.013 g, 0.044 mmol) was dissolved in 5 mL of dry methylene chloride. The solution was cooled in ice/water bath and then oxalyl chloride (0.02 mL, 0.2 mmol) was added to the solution followed by adding of one drop of DMF as a catalyst. After 15 min the reaction mixture was evaporated in vacuum and the residue was re-evaporated from toluene. The resulting acyl chloride 7 was dissolved in 5 mL of dry methylene chloride and added to the solution of phenol 6 (0.016 g, 0.045 mmol) in 3 mL of DMF, containing DIEA (0.039 mL, 0.22 mmol). The reaction mixture was stirred for 30 min at RT and then diluted with 10% HCl (50 mL). The product was extracted with ethyl acetate (2×20 mL). The combined extract was washed with brine (30 mL), dried over $Na_2SO_4$ and evaporated. The crude product was purified by column chromatography using 100:10:0.5 chloroform-methanol-acetic acid as an eluant to give phenol ester 8 (0.010 g, 36%) as an orange solid.

Example 3. BODIPY Ester of 2,6-Difluoro Activated Phenol, Solubilized with Two Carboxylic Groups (Compound 10)

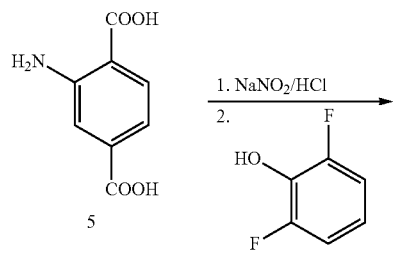

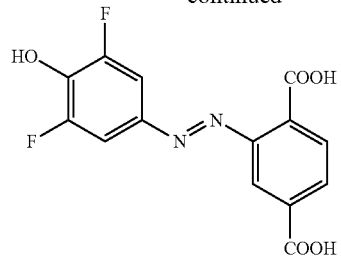

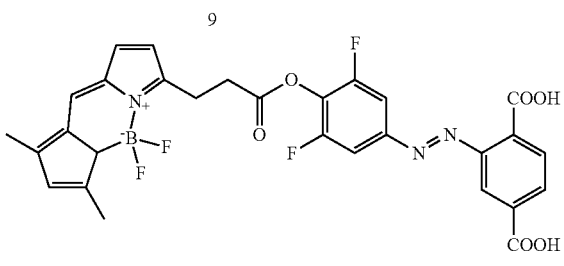

2-((3,5-Difluoro-4-hydroxyphenyl)diazenyl)terephthalic acid (9)

2-Aminoterephtalic acid (1.00 g, 5.52 mmol) was dissolved in hot mixture of 60 mL of water and 20 mL of conc. HCl. The solution was cooled in ice/NaCl bath to 0° C. giving a suspension of HCl salt. The solution of sodium nitrite (0.460 g, 6.67 mmol in 10 mL of water) was added dropwise to the suspension of ammonium salt, maintaining the temperature below +5° C. The resulting solution was stirred for 20 min and then added dropwise to the solution of 2,6-difluorophenol (0.720 g, 5.53 mmol) in 50 mL of 1M KOH, cooled in ice/water bath. The reaction mixture was stirred for 1.5 hrs in ice/water bath and then acidified with 10% HCl to pH 2-3. The resulting precipitate was collected, washed with water and dried in vacuum to give phenol 9 as an orange solid (0.5 g, 28%).

3-(3-(2,6-Difluoro-4-((2,5-dicarboxyphenyl)diazenyl)phenoxy)-3-oxopropyl)-5,5-difluoro-7,9-di methyl-5H-di pyrrol o[1,2-c:1',2'-f][1,3,2]diazaborinin-4-ium-5-uide (10)

3-(2-Carboxyethyl)-5,5-difluoro-7,9-dimethyl-5H-dipyrrolo[1,2-c:1',2'-f][1,3,2]diazaborinin-4-ium-5-uide (3, 0.020 g, 0.068 mmol) was dissolved in 5 mL of dry methylene chloride. The solution was cooled in ice/water bath and then oxalyl chloride (0.03 mL, 0.34 mmol) was added to the solution followed by adding one drop of DMF as a catalyst. After 15 min the reaction mixture was evaporated in vacuum and the residue was re-evaporated from toluene. The resulting acyl chloride 7 was dissolved in 5 mL of dry methylene chloride and added to the solution of phenol 9 (0.022 g, 0.068 mmol) in 3 mL of DMF, containing DIEA (0.060 mL, 0.34 mmol). The reaction mixture was stirred for 30 min at RT and then diluted with 50 mL of ethyl acetate. The mixture was washed with 10% HCl (3×20 mL), brine (30 mL), dried over $Na_2SO_4$ and evaporated. The crude product was purified by column chromatography using 100:10:0.5 chloroform-methanol-acetic acid as an eluant to give phenol ester 10 (0.020 g, 49%) as an orange solid.

Example 4. BODIPY Ester of 2,6-Difluoro Activated Phenol, Solubilized with Triethyleneglycol Substituent (Compound 20)

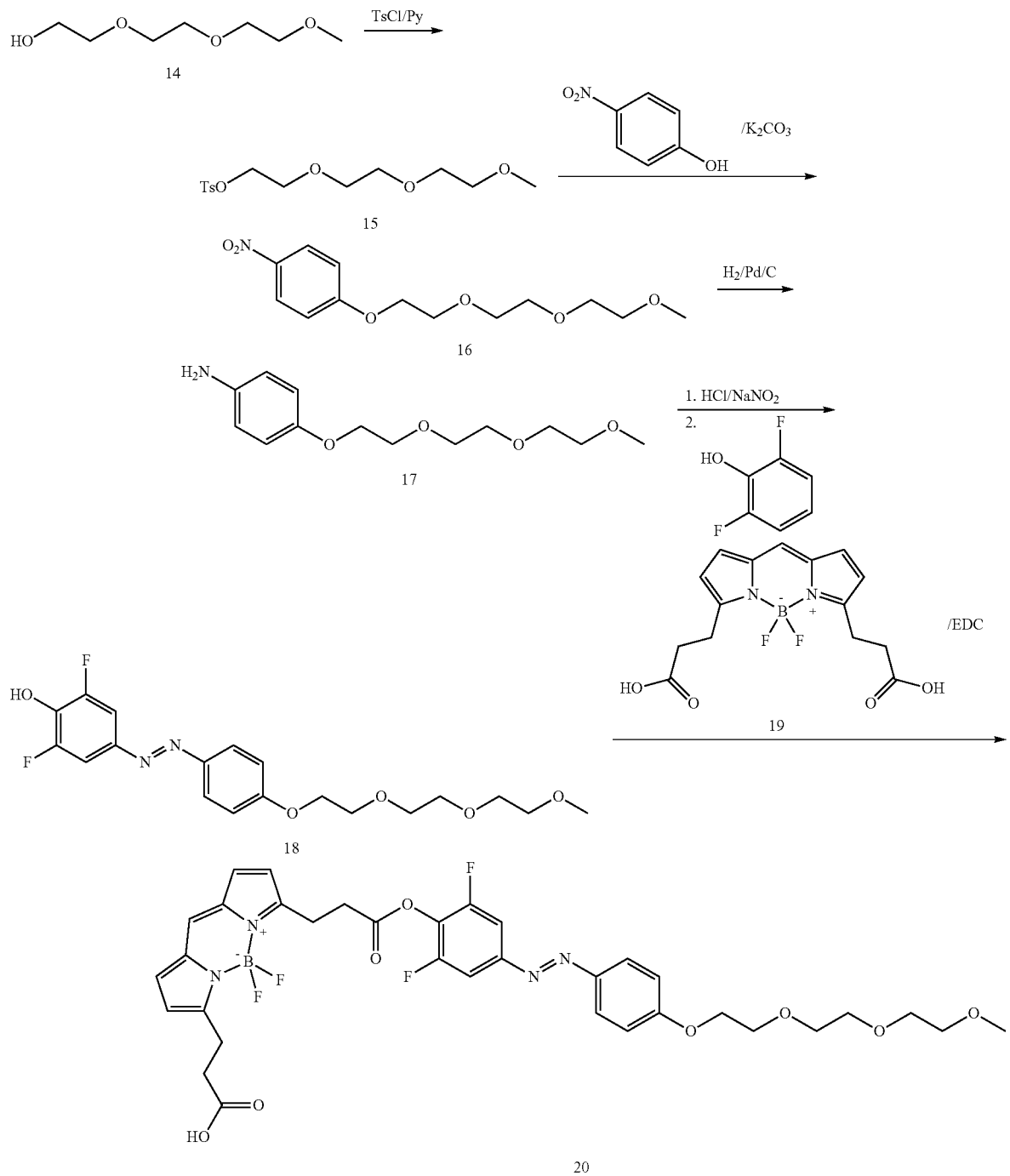

2-(2-(2-methoxyethoxy)ethoxy)ethyl 4-methylbenzenesulfonate (15)

Triethylene glycol monomethyl ether (14, 2.00 mL, 12.8 mmol) was dissolved in 5 mL of pyridine and the solution was cooled in ice/water bath. Tosyl chloride was added portionwise to the solution of 14 and the reaction mixture was stirred for 30 min in ice/water bath. The n it was diluted with 100 mL of toluene and evaporated. The residue was mixed with 30 mL of 10% HCl and the product was extracted with ethyl acetate (3×30 mL). The combined extract was washed with water (30 mL), brine (30 mL), dried over $Na_2SO_4$ and evaporated to give tosylate 15 as a clear oil (3.50, 86%).

1-(2-(2-(2-methoxyethoxy)ethoxy)ethoxy)-4-nitrobenzene (16)

Tosylate 15 (1.14 g, 3.58 mmol) and p-nitrophenol (0.50 g, 3.6 mmol) were dissolved in 20 mL of acetonitrile. Powdered $K_2CO_3$ (0.50 g, 3.6 mmol) was added to the solution and the mixture was stirred overnight under reflux. Then the mixture was cooled to rt and diluted with 50 mL of water. The product was extracted with ethyl acetate (3×30 mL). The combined extract was washed with water (2×30 mL), brine (30 mL), dried with $Na_2SO_4$ and evaporated to give 16 (0.94 g, 90%) as a clear oil.

4-(2-(2-(2-methoxyethoxy)ethoxy)ethoxy)aniline (17)

Nitro compound 17 (1.01 g, 3.54 mmol) was dissolved in 30 mL of methylene chloride. 10% Palladium on carbon (100 mg) was added and the reaction mixture was shaken at 40 psi of hydrogen in Parr apparatus for 2 hrs. The reaction mixture was filtered from the catalyst and evaporated. The crude product was purified by chromatography on silica gel column using 2:1 ethyl acetate-chloroform mixture as an eluant to give aniline 17 as a dark oil (0.436 g, 48%).

2,6-difluoro-4-((4-(2-(2-(2-methoxyethoxy)ethoxy)ethoxy)phenyl)diazenyl)phenol (18)

4-(2-(2-(2-methoxyethoxy)ethoxy)ethoxy)aniline (17) (0.436 g, 1.71 mmol) was dissolved in hot mixture of 20 mL of water and 0.5 mL of conc. HCl. The solution was cooled in ice/NaCl bath to 0° C. and then the solution of sodium nitrite (0.140 g, 2.03 mmol in 4 mL of water) was added dropwise to the solution of ammonium salt, maintaining the temperature below +5° C. The resulting solution of diazonium salt was stirred for 30 min and then added dropwise to the solution of 2,6-difluorophenol (0.220 g, 1.69 mmol) in 10 mL of 1M KOH, cooled in ice/water bath. The reaction mixture was stirred for 40 min in ice/water bath and then acidified with 10% HCl to pH 2-3 and extracted with ethyl acetate (4×40 mL). The combined extract was washed with brine (30 mL), dried over $Na_2SO_4$ and evaporated. The crude product was purified by column chromatography on silica gel using 2:1 chloroform-ethyl acetate mixture as an eluant to give phenol 18 as a orange solid (0.094 g, 14%).

7-(2-carboxyethyl)-3-(3-(2,6-difluoro-4-((4-(2-(2-(2-methoxyethoxy)ethoxy)ethoxy)phenyl)diazenyl)phenoxy)-3-oxopropyl)-5,5-difluoro-5H-dipyrrolo[1,2-c:1',2'-f][1,3,2]diazaborinin-4-ium-5-uide (20)

3,7-Bis(2-carboxyethyl)-5,5-difluoro-5H-dipyrrolo[1,2-c:1',2'-f][1,3,2]diazaborinin-4-ium-5-uide (19, 0.035 g, 0.11 mmol) and phenol 18 (0.046 g, 0.12 mmol) were dissolved in the mixture of 1 mL of DMF and 1 mL of acetonitrile. EDC (0.022 g, 0.12 mmol) was added to solution and the reaction mixture was stirred overnight at rt and then evaporated in vacuum. The crude product was purified by column chromatography on silica gel using 100:100:0.5 chloroform-ethyl acetate-acetic acid mixture to give ester 20 as an orange solid (0.040 g, 51%).

Example 5

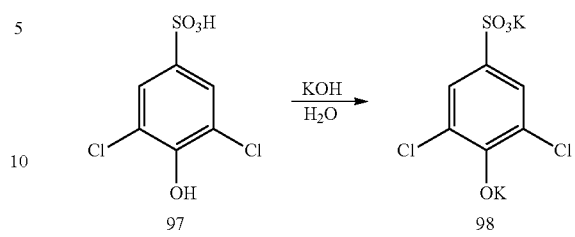

To a 1 M solution of potassium hydroxide (20.8 ml, 0.0208 mol) was added 3,5-dichloro-4-hydroxybenzenesulfonic acid (97) (2.553 g, 0.0105 mol) and the purple solution was stirred at room temperature for 1 hour. The reaction mixture was filtered through a pipette containing a glass wool plug to remove any remaining brown solids. The filtrate was frozen on dry ice and lyophilized to give 3.04 g (91% yield) of 98 as a light purple solid.

Example 6

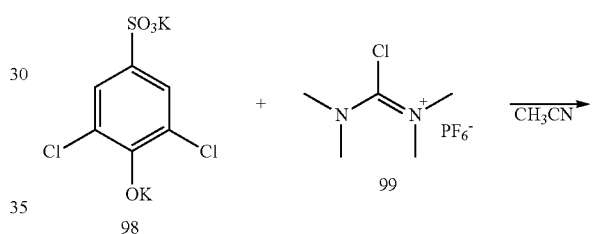

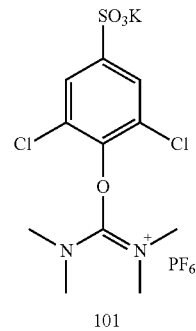

To a suspension of 98 (300 mg, 0.942 mmol) in anhydrous acetonitrile was added 99 (264 mg, 0.942 mmol), and the suspension was stirred under argon at room temperature for 18 hours. The reaction mixture was centrifuged to remove the precipitate and the supernatant was decanted and evaporated in vacuo. Fresh acetonitrile (3 ml) was added and the resulting solution added dropwise to a stirred solution of ether (60 ml) to give a white precipitate. The precipitate was allowed to settle and the ether decanted. Fresh ether (60 ml) was added, stirred, allowed to settle, and decanted two more times. The resulting white precipitate was dried under high vacuum to give 338 mg (70% yield) of 101 as a white powder.

Example 7

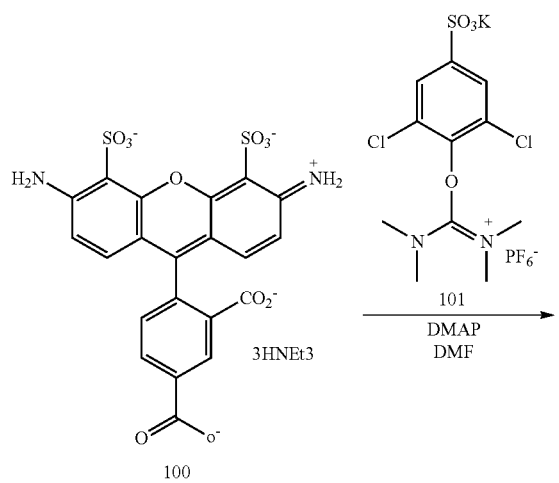

To a mixture of compound 100 (350 mg, 0.418 mmol) and DMAP (51 mg, 0.418 mmol) in anhydrous DMF (35 ml) was added 4-oxa-(potassium 3,5-dichloro-4-oxidobenzenesulfonate) tetramethyluronium hexafluorophosphate (101) (255 mg, 0.501 mmol) to give an orange suspension that was stirred at room temperature under argon for 24 hrs. The reaction mixture was added dropwise to stirring ethyl acetate (350 ml). The mixture was centrifuged and the supernatant removed. Additional ethyl acetate (300 ml) was added and the precipitate resuspended, then centrifuged and the supernatant removed. This was repeated 2 more times. Acetonitrile (300 ml) was then added and the precipitate resuspended, then centrifuged and the supernatant removed. Purification by silica gel chromatography (acetonitrile:water, 98:2 to 92:8) afforded 217 mg (63% yield) of 102 as a dark orange solid.

Example 8

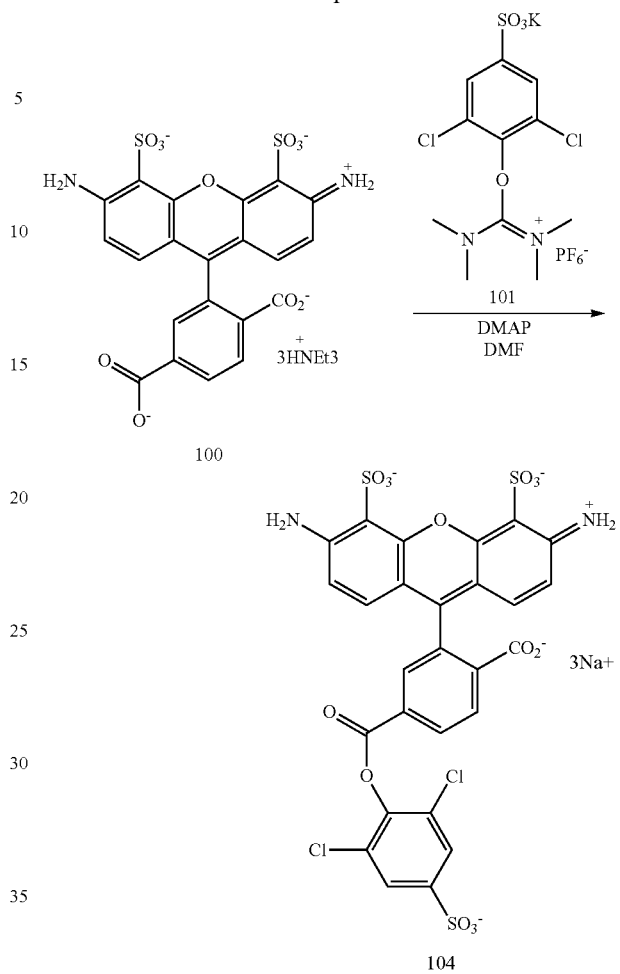

To a mixture of Compound 103 (50 mg, 0.0597 mmol) and DMAP (1 mg) in anhydrous DMF (5 ml) was added 4-oxa-(potassium 3,5-dichloro-4-oxidobenzenesulfonate) tetramethyluronium hexafluorophosphate (101) (60 mg, 0.119 mmol) to give an orange suspension that was stirred at room temperature under argon for 6 days. The reaction mixture was added dropwise to stirring ethyl acetate (30 ml). The mixture was centrifuged and the supernatant removed. Additional ethyl acetate (30 ml) was added and the precipitate resuspended, then centrifuged and the supernatant removed. Purification by silica gel chromatography (acetonitrile:water, 95:5 to 90:10) afforded 10 mg (15% yield) of 104 as a dark orange solid.

Example 9

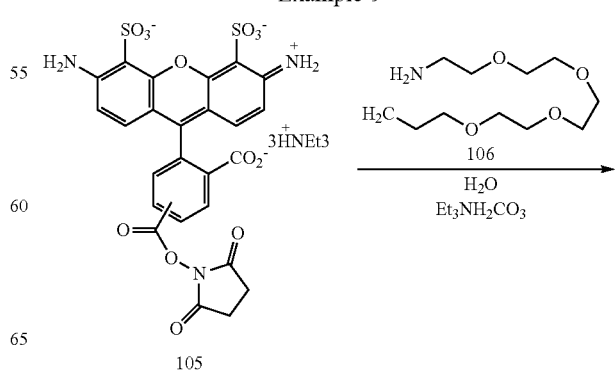

55
-continued

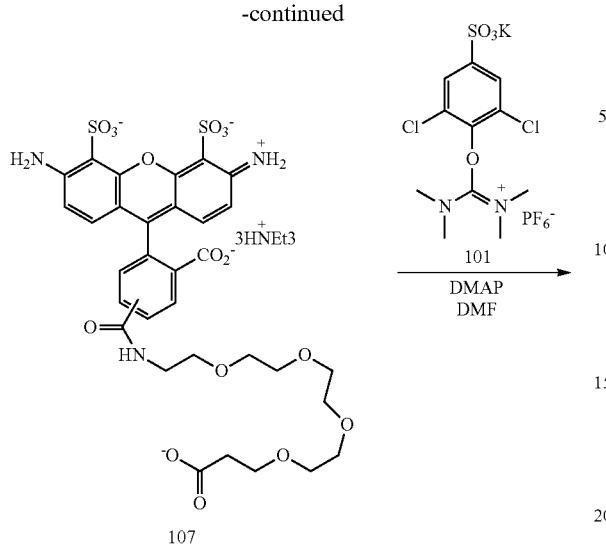

107

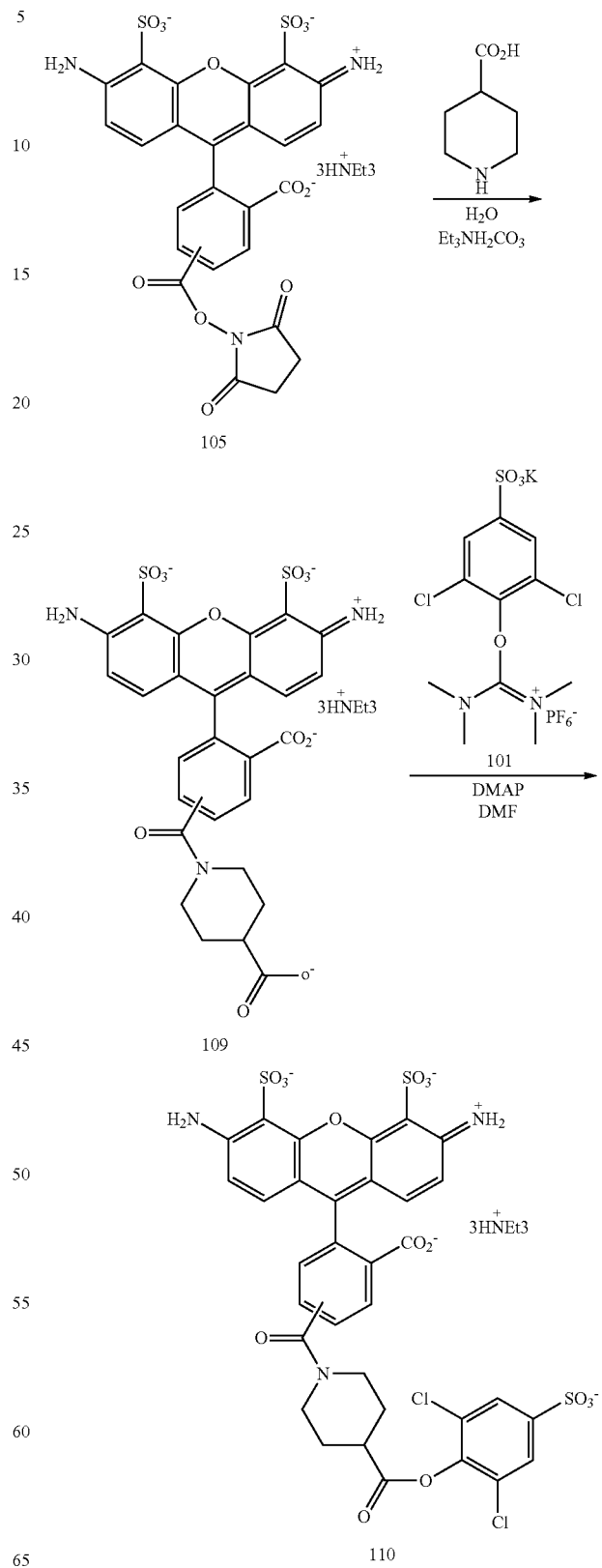

108

To a mixture of amino-dPEG₄-acid (106) (14 mg, 0.054 mmol) and 1 M triethylammonium bicarbonate (0.18 ml, 0.18 mmol) in water (0.5 ml) was added Compound 105 (30 mg, 0.036 mmol) and the reaction was stirred at room temperature for 2 hours. The solvent was evaporated in vacuo, water (2 ml) added and evaporated, and this was repeated twice more. Purification by LH-20 column (eluent: water) afforded 15 mg (41% yield) of 107 as an orange solid.

To a mixture of 107 (12 mg, 0.012 mmol) and DMAP (1 mg) in anhydrous DMF (1 ml) was added 4-oxa-(potassium 3,5-dichloro-4-oxidobenzenesulfonate) tetramethyluronium hexafluorophosphate (101) (14 mg, 0.026 mmol). The reaction mixture was stirred for 3 hours at room temperature under argon, and the solvent was removed in vacuo. Acetonitrile (3 ml) was added and the suspension was sonicated and stirred, then centrifuged and the supernatant removed. This was repeated 3 times. Purification by silica gel chromatography (acetonitrile:water, 8:2) afforded 108 as an orange solid.

56
Example 10

To a mixture of isonipecotic acid (7 mg, 0.054 mmol) and 1 M triethylammonium bicarbonate (0.18 ml, 0.18 mmol) in water (0.5 ml) was added Compound 105 (30 mg, 0.036 mmol) and the reaction was stirred at room temperature for 24 hours. The solvent was evaporated in vacuo, water (2 ml) added and evaporated, and this was repeated twice more. Purification by LH-20 column (eluent: water) afforded 13 mg (43% yield) of 109 as an orange solid.

To a mixture of 109 (17 mg, 0.020 mmol) and DMAP (1 mg) in anhydrous DMF (1 ml) was added 4-oxa-(potassium 3,5-dichloro-4-oxidobenzenesulfonate) tetramethyluronium hexafluorophosphate (101) (11 mg, 0.022 mmol). The reaction mixture was stirred for 2 hours at room temperature under argon, and the solvent was removed in vacuo. Acetonitrile (3 ml) was added and the suspension was sonicated and stirred, then centrifuged and the supernatant removed. This was repeated 3 times. Residual solvent was removed in vacuo to provide 110 as an orange solid.

Example 11

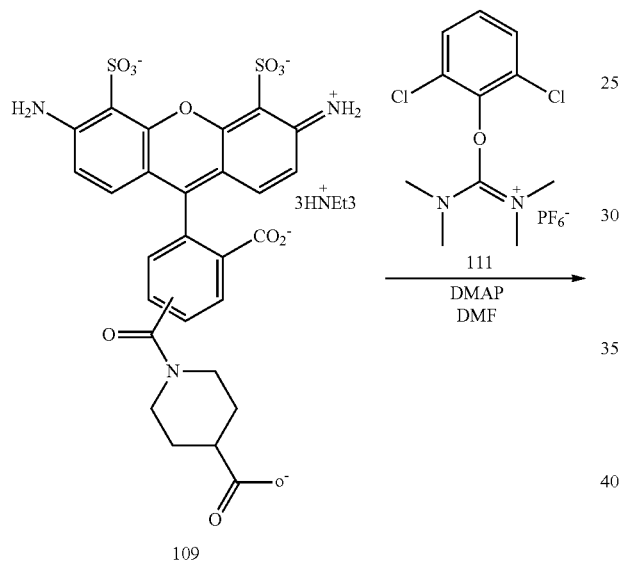

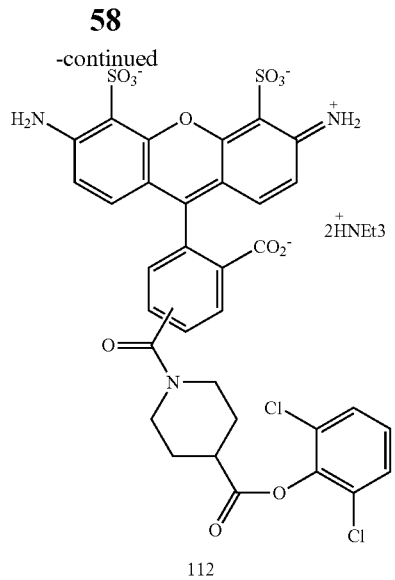

To a mixture of 109 (7 mg, 0.0079 mmol) and DMAP (1 mg) in anhydrous DMF (1 ml) was added O-(1,3-dichloro-2-oxidobenzene) tetramethyluronium hexafluorophosphate (111) (8 mg, 0.019 mmol). The reaction mixture was stirred for 24 hours at room temperature under argon, and the solvent was removed in vacuo. Purification by silica gel chromatography (acetonitrile:water, 8:2) afforded 3 mg (38% yield) of 112 as an orange solid.

Example 12

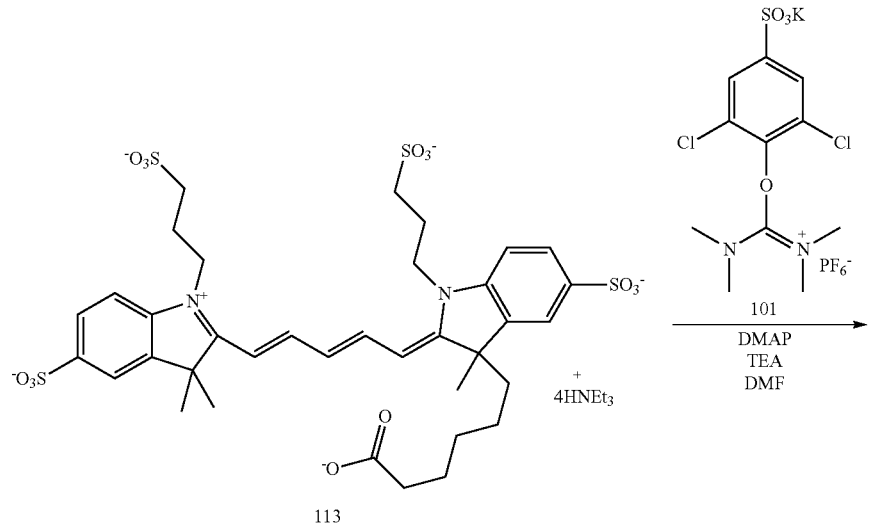

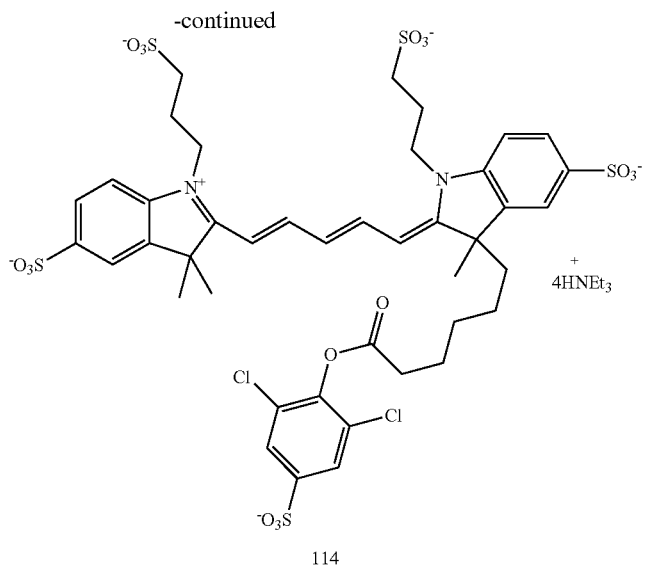

114

To a mixture of Compound 113 (100 mg, 0.086 mmol), DMAP (10.5 mg, 0.086 mmol) and triethylamine (27 mg, 0.267 mmol) in anhydrous DMF (10 ml) was added 4-oxa-(potassium 3,5-dichloro-4-oxidobenzenesulfonate) tetramethyluronium hexafluorophosphate (101) (53 mg, 0.103 mmol) to give a blue solution that was stirred at room temperature under argon for 24 hrs. The reaction mixture was added dropwise to stirring ethyl acetate (100 ml). The mixture was centrifuged and the supernatant removed. Additional ethyl acetate (100 ml) was added and the precipitate resuspended, then centrifuged and the supernatant removed. This was repeated 2 more times. Acetone (100 ml) was then added and the precipitate resuspended, then centrifuged and the supernatant removed. Removal of excess solvent in vacuo provided 82 mg (65% yield) of 114 as a blue solid.

Example 13

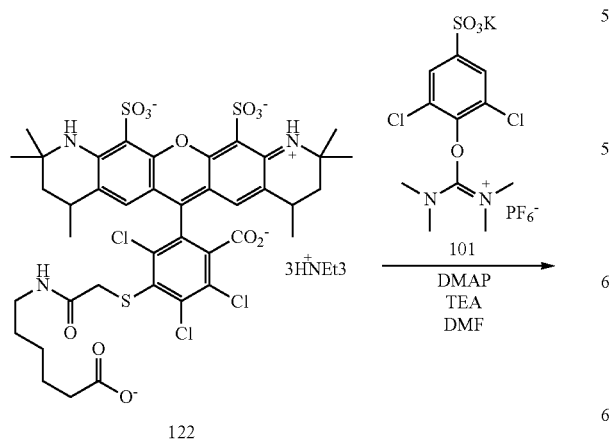

122

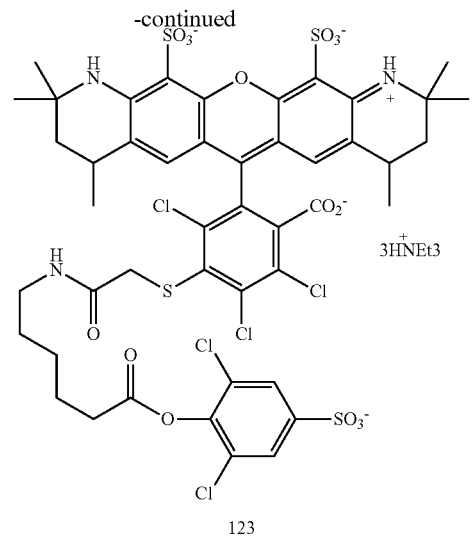

123

Combine Compound 122 (0.10 mmol), DMAP (0.10 mmol), and triethylamine (0.14 mmol) in anhydrous DMF (10 ml). Add 4-oxa-(potassium 3,5-dichloro-4-oxidobenzenesulfonate) tetramethyluronium hexafluorophosphate (101) (0.11 mmol) and stir the reaction mixture at room temperature under argon for 24 hrs. Add the reaction mixture dropwise to stirring ethyl acetate to precipitate the product and centrifuge the suspension to isolate the product. Purify by silica gel column chromatography using acetonitrile/water as the eluent to afford 123 as a red solid.

Example 14

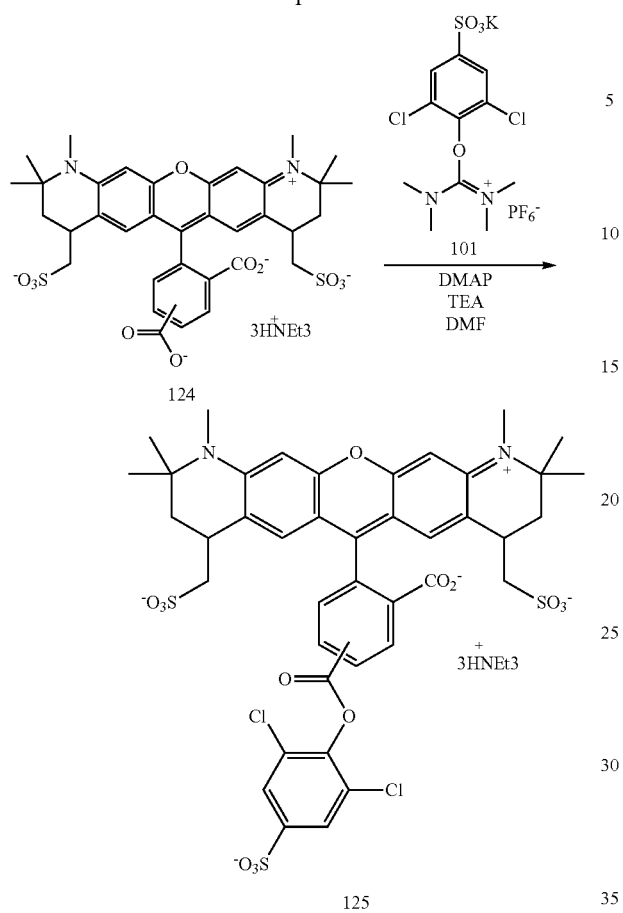

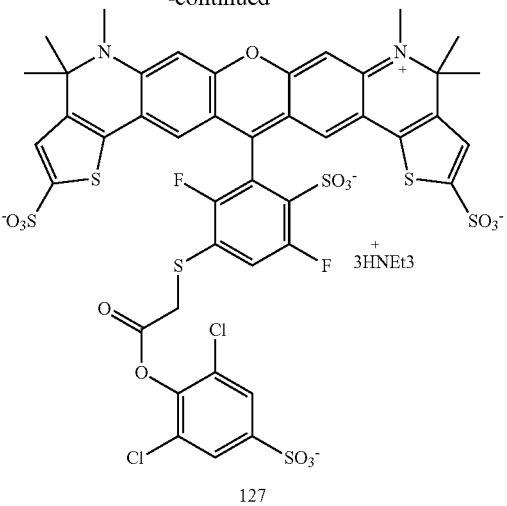

Combine Compound 124 (0.10 mmol), DMAP (0.10 mmol), and triethylamine (0.29 mmol) in anhydrous DMF (10 ml). Add 4-oxa-(potassium 3,5-dichloro-4-oxidobenzenesulfonate) tetramethyluronium hexafluorophosphate (101) (0.13 mmol) and stir the reaction mixture at room temperature under argon for 24 hrs. Add the reaction mixture dropwise to stirring ethyl acetate to precipitate the product and centrifuge the suspension to isolate the product. Purify by silica gel column chromatography using acetonitrile/water as the eluent to afford 125 as a purple solid.

Example 15

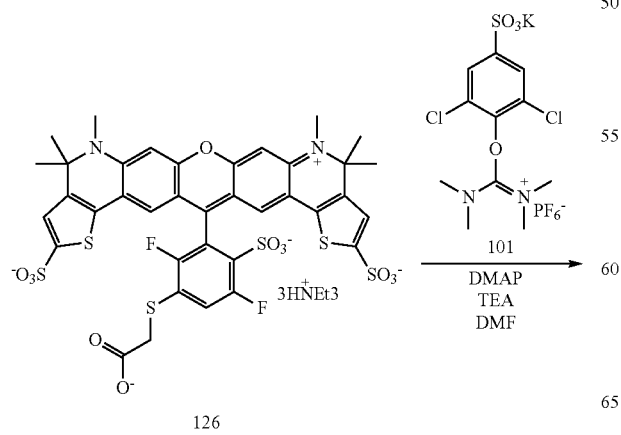

Combine Compound 126 (0.10 mmol) and DMAP (0.10 mmol) in anhydrous DMF (10 ml). Add 4-oxa-(potassium 3,5-dichloro-4-oxidobenzenesulfonate) tetramethyluronium hexafluorophosphate (101) (0.30 mmol) and stir the reaction mixture at room temperature under argon for 24 hrs. Add the reaction mixture dropwise to stirring ethyl acetate to precipitate the product and centrifuge the suspension to isolate 127 as a blue solid.

Example 16

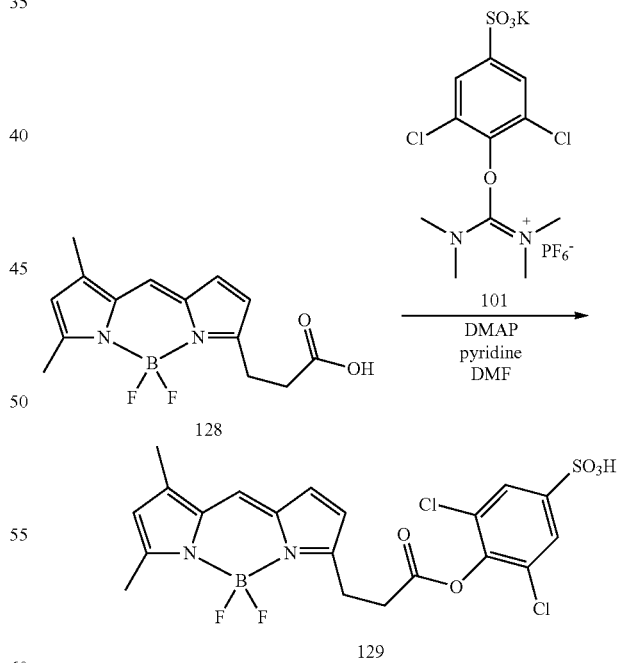

Combine BODIPY FL carboxylic acid (128) (0.10 mmol), DMAP (0.10 mmol) and anhydrous pyridine (0.20 mmol) in anhydrous DMF (10 ml). Add 4-oxa-(potassium 3,5-dichloro-4-oxidobenzenesulfonate) tetramethyluronium hexafluorophosphate (101) (0.20 mmol) and stir the reaction mixture at room temperature under argon for 24 hrs. Add the reaction mixture dropwise to stirring ethyl acetate to precipitate the product and centrifuge the suspension to isolate 129 as an orange solid.

Example 17

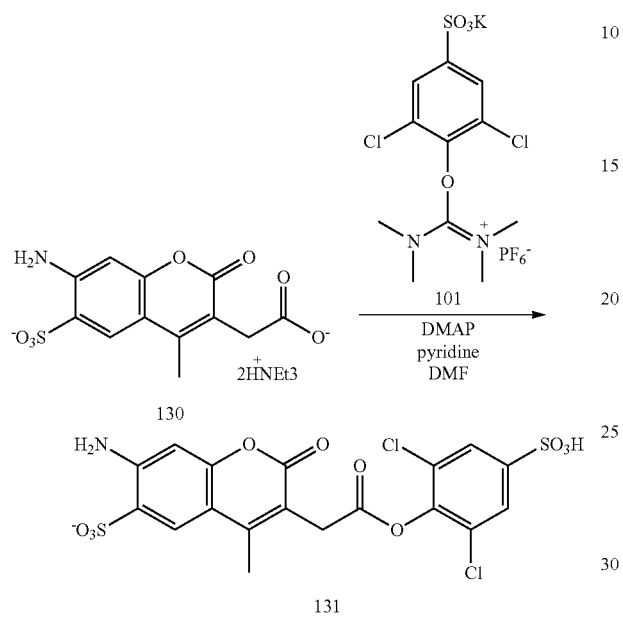

Combine Compound 130 (0.10 mmol), DMAP (0.10 mmol), and triethylamine (0.20 mmol) in anhydrous DMF (10 ml). Add 4-oxa-(potassium 3,5-dichloro-4-oxidobenzenesulfonate) tetramethyluronium hexafluorophosphate (101) (0.20 mmol) and stir the reaction mixture at room temperature under argon for 24 hrs. Add the reaction mixture dropwise to stirring ethyl acetate to precipitate the product. Decant the ethyl acetate and add 4 M HCl in dioxane with stirring. Centrifuge the suspension to collect the precipitate and isolate 131 as a light yellow solid.

Example 18

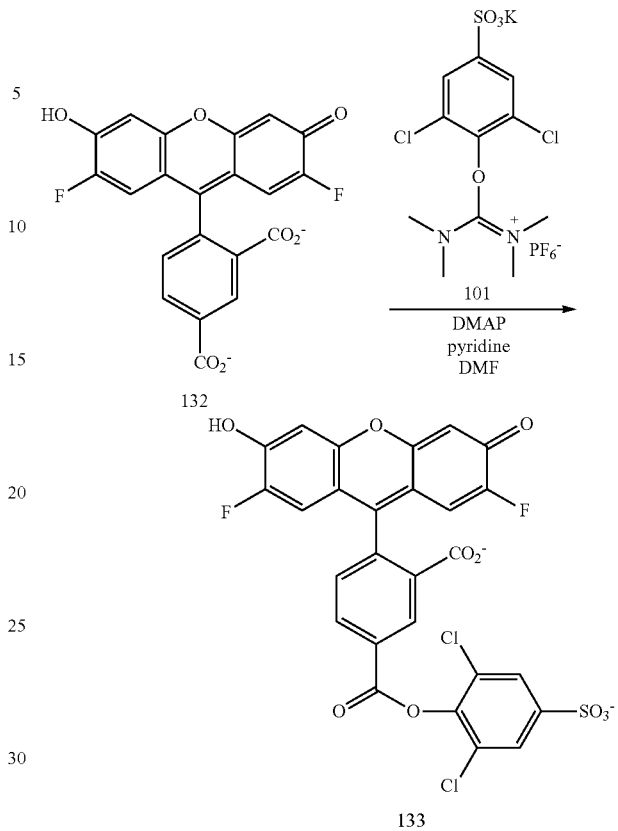

Combine Oregon Green carboxylic acid (132) (0.10 mmol), DMAP (0.10 mmol) and anhydrous pyridine (0.20 mmol) in anhydrous DMF (10 ml). Add 4-oxa-(potassium 3,5-dichloro-4-oxidobenzenesulfonate) tetramethyluronium hexafluorophosphate (101) (0.12 mmol) and stir the reaction mixture at room temperature under argon for 24 hrs. Add the reaction mixture dropwise to stirring ethyl acetate to precipitate the product and centrifuge the suspension to isolate 133 as a yellow solid.

Example 19

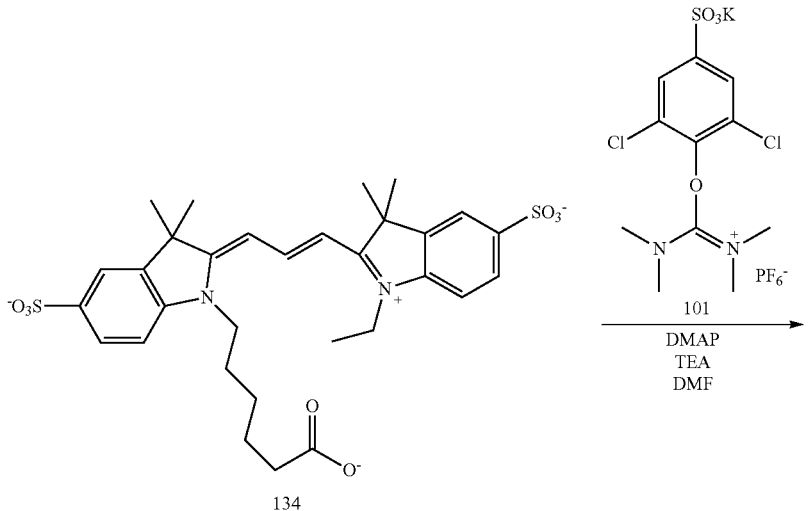

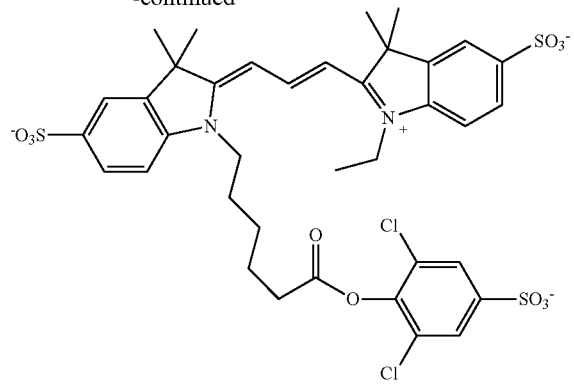

135

Combine Cy3 carboxylic acid (134) (0.10 mmol), DMAP (0.10 mmol), and triethylamine (0.31 mmol) in anhydrous DMF (10 ml). Add 4-oxa-(potassium 3,5-dichloro-4-oxidobenzenesulfonate) tetramethyluronium hexafluorophosphate (101) (0.12 mmol) and stir the reaction mixture at room temperature under argon for 24 hrs. Add the reaction mixture dropwise to stirring ethyl acetate to precipitate the product and centrifuge the suspension to isolate 135 as a purple solid.

Example 20

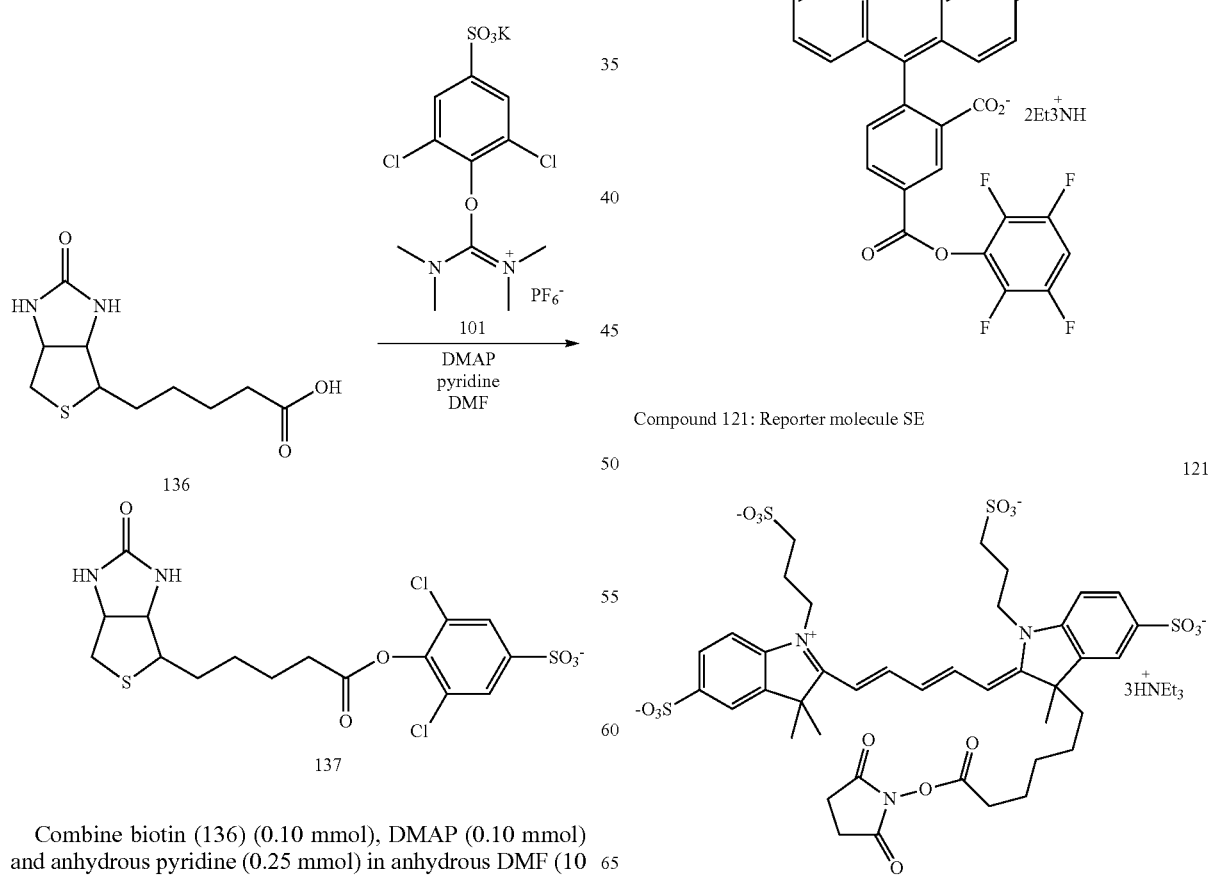

Combine biotin (136) (0.10 mmol), DMAP (0.10 mmol) and anhydrous pyridine (0.25 mmol) in anhydrous DMF (10 ml). Add 4-oxa-(potassium 3,5-dichloro-4-oxidobenzenesulfonate) tetramethyluronium hexafluorophosphate (101) (0.16 mmol) and stir the reaction mixture at room temperature under argon for 24 hrs. Add the reaction mixture dropwise to stirring ethyl acetate to precipitate the product and centrifuge the suspension to isolate 133 as a colorless solid.

Compound 120 Reporter molecule TFP

Compound 121: Reporter molecule SE

-continued

Compound 122: Labeled DCP

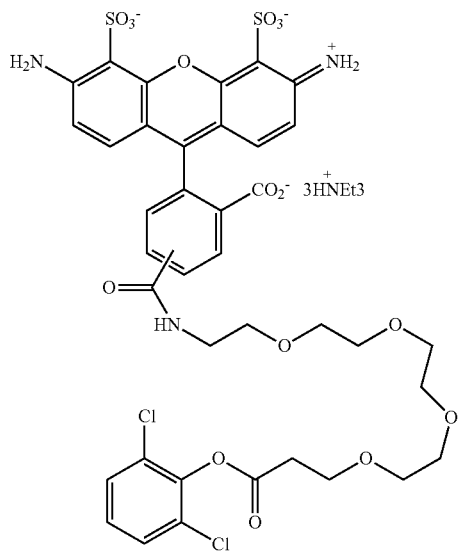

Results:

Samples were incubated at room temperature in the indicated solution. Aliquots were taken at 1, 2, 3, 4 and 24 hrs and analyzed by HPLC to determine percent hydrolysis, from which the average half-life was determined.

TABLE 1

Hydrolysis Half-Life Data

| Compound | E-pure $H_2O$ pH ~5 | DMSO | 25 mM phosphate buffer pH 8.6 |
|---|---|---|---|
| Compound 102 | 21 days | 16 days | 28 hrs |
| Compound 104 | — | — | 17 hrs |
| Compound 105 | — | — | 74 min |
| Compound 120 | — | — | 78 min |
| Compound 108 | — | — | 6 hrs |
| Compound 110 | — | — | 1.5 hrs |
| Compound 112 | — | — | 122 hrs |
| Compound 122 | — | — | 16 hrs |
| Compound 114 | — | — | 102 min |
| Compound 121 | — | — | 105 min |

Samples were incubated at room temperature in the indicated solution. Aliquots were taken at 1, 2, 3, 4 and 24 hrs and analyzed by HPLC to determine percent hydrolysis, from which the average half-life was determined. Results are shown in Table 2.

TABLE 2

Hydrolysis Half-Life Data in Various Buffer Solutions

| | Compound 102 | Compound 105 | Compound 120 |
|---|---|---|---|
| 25 mM phosphate buffer pH 8.6 | 28 hrs | 74 min | 78 min |
| 10 mM HEPES buffer pH 8.2, 0.2M NaCl | 159 hrs | 4 hrs | 6.5 hrs |
| 20 mM Tris buffer pH 8.6 | 77 hrs | 12 min | 139 min |
| 25 mM Borate buffer pH 8.6 | 3.5 hrs | <5 min | <5 min |

TABLE 2-continued

Hydrolysis Half-Life Data in Various Buffer Solutions

| | Compound 102 | Compound 105 | Compound 120 |
|---|---|---|---|
| 25 mM phosphate buffer pH 7.2 | 245 hrs | 111 min | 173 min |
| 20 mM Tris buffer pH 7 | 1019 hrs | 244 min | 836 min |
| 25 mM phosphate buffer pH 8.6 w/10 mM imidazole | 38 min | <2 min | <2 min |
| 20 mM Tris buffer pH 8.6 w/50 mM $NaN_3$ | 95 min | <1 min | <1 min |

Samples were incubated with Compound 102 at room temperature for 1 hour in the designated buffer. Antibody labeling occurs in each buffer system. Results are shown in Table 3.

TABLE 3

Goat anti-Mouse Antibody Degree of Labeling with Compound 102

| | Molar Ratio 5 | Molar Ratio 10 | Molar Ratio 15 | Molar Ratio 20 |
|---|---|---|---|---|
| 25 mM phosphate buffer pH 8.6 | 4.5 | 7.5 | 10.0 | 12.6 |
| 10 mM HEPES buffer pH 8.2, 0.2M NaCl | 2.1 | 3.2 | 4.8 | 5.0 |
| 20 mM Tris buffer pH 8.6 | 2.2 | 3.0 | 3.5 | 3.8 |

Samples were incubated with Compound 102 at a molar ratio of 12 in the designated buffer at room temperature for the specified incubation time. Higher degrees of labeling are possible with longer incubation times, depending on the buffer system. Results are shown in Table 4.

TABLE 4

Degree of Antibody Labeling at Long Incubation Times with Compound 102

| | Degree of Labeling | Incubation Time |
|---|---|---|
| 25 mM phosphate buffer pH 8.6 | 8.9 | 3 hrs |
| 25 mM phosphate buffer pH 7.2 | 6.5 | 6 hrs |
| 10 mM HEPES buffer pH 8.2, 0.2M NaCl | 8.6 | 20 hrs |
| 20 mM Tris buffer pH 8.6 | 7.5 | 12 hrs |

2-(6-amino-3-iminio-4,5-disulfonato-3H-xanthen-9-yl) benzoate, comprising an SDP ester was prepared and compared to commercially available 2-(6-amino-3-iminio-4,5-disulfonato-3H-xanthen-9-yl)benzoate comprising a succinimidyl ester (SE) and 2-(6-amino-3-iminio-4,5-disulfonato-3H-xanthen-9-yl)benzoate comprising a TFP for hydrolytic stability in 25 mM Pi buffer pH 8.6. The SE compound had a half-life of 74 min and TFP had a half-life of 78 min, while the SDP had a half-life of 28 hours. This dramatic increase in hydrolytic stability has significant impact on the preparation and purification, ease of handling, storage stability, and biomolecule labeling efficiency. After preparation of the SDP, the crude compound was purified to 98% purity by silica gel flash chromatography using acetonitrile/water as the eluent. Purification is not possible with SE (prepared and sold in 50-70% purity) or TFP (prepared and sold in 50-80% purity) because of their hydrolytic instability. The SDP is also stable to lyophylization which greatly increases the ease of handling and packaging. With greater hydrolytic stability also comes less degradation upon storage than Compound 120 and Compound 105. In addition, with more hydrolytic stability comes greater labeling efficiency, with AF488 SDP giving nearly twice as much biomolecule labeling as an equivalent amount of Compound 105.

Each of the above-cited references are hereby incorporated by reference as if set forth fully herein.

The invention claimed is:

1. A method of making a compound of Formula I comprising:

contacting a carrier molecule or a solid support comprising a nucleophile with a compound of Formula IA or a tautomer or salt thereof:

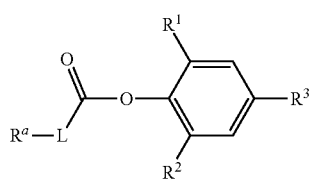

wherein,
L is a linker;
$R^1$ is chlorine;
$R^2$ is chlorine;
$R^3$ is COO$^-$, SO3$^-$, substituted azenyl, PEG, phosphate or bisphosphonate; and
$R^a$ is a reporter molecule;
forming a compound of Formula I or a tautomer or salt thereof:

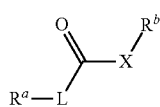

wherein
L is the linker;
$R^a$ is the reporter molecule; and
$R^b$ is the carrier molecule or solid support comprising a nucleophile (X).

2. The method of claim 1, wherein X is —NH, —S— or —O—.

3. The method of claim 1, wherein L is a covalent bond, -alkyl-, -substituted alkyl-, -alkenyl-, -substituted alkenyl-, -heterocyclyl-, -substituted heterocyclyl-, -aryl-, -substituted aryl-, -heteroaryl-, -substituted heteroaryl-, -cycloakyl-, -substituted cycloalkyl-, -oxy-, -alkoxy-, -substituted alkoxy-, -thio-, -amino-, or -substituted amino-.

4. The method of claim 1, wherein $R^a$ is a dye.

5. The method of claim 4, wherein the dye is a xanthene, a cyanine, an indole, a benzofuran, a coumarin, or a borapolyazaindacine.

6. The method of claim 1, wherein the reporter molecule $R^a$ is an ion chelating moiety, a hapten, an antibody, an enzyme, a radiolabel, a metal ion or metal ion containing substance, a pigment, a chromogen, a phosphor, a fluorogen, a bioluminescent substance, a chemiluminescent substance, or a semiconductor nanocrystal.

7. The method of claim 1, wherein $R^b$ is a solid support.

8. The method of claim 1, wherein $R^b$ is a carrier molecule.

9. The method of claim 8, wherein the carrier molecule is selected from the group consisting of an amino acid, a peptide, a protein, a carbohydrate, a polysaccharide, a nucleoside, a nucleotide, an oligonucleotide, a nucleic acid polymer, a drug, a lipid, and a synthetic polymer.

10. The method of claim 1, wherein the compound of Formula IA is a salt.

11. The method of claim 10, wherein the salt comprises a potassium or sodium ion.

12. The method of claim 1, further comprising incubating the carrier molecule or solid support with the compound of Formula IA after the contacting step.

13. The method of claim 1, wherein the contacting step is done in an aqueous solution.

14. The method of claim 1, wherein the reporter molecule is hydrophobic.

15. The method of claim 1, wherein the compound of Formula IA is soluble in an aqueous solution.

16. A method of labeling a carrier molecule or solid support comprising:

contacting the carrier molecule or solid support with a compound of Formula IA or a tautomer or salt thereof:

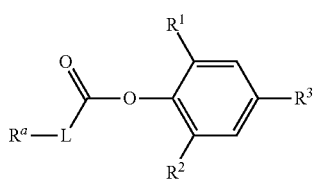

wherein,
L is a linker;
$R^1$ is chlorine;
$R^2$ is chlorine;
$R^3$ is COO$^-$, SO3$^-$, substituted azenyl, PEG, phosphate or bisphosphonate; and
$R^a$ is a reporter molecule; and
the carrier molecule or solid support comprises a nucleophile; and
forming a labeled carrier molecule or solid support.

17. The method of claim 16, wherein the labeled carrier molecule or solid support comprises a compound of Formula I:

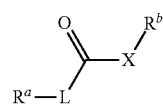

wherein,
$R^a$ is the reporter molecule; and
$R^b$ is the carrier molecule or solid support comprising a nucleophile (x).

* * * * *